US006337335B1

(12) United States Patent
Hutchings et al.

(10) Patent No.: US 6,337,335 B1
(45) Date of Patent: *Jan. 8, 2002

(54) SUBSTITUTED 2-ANILINOPYRIMIDINES USEFUL AS PROTEIN KINASE INHIBITORS

(75) Inventors: Martin Clive Hutchings, Berkshire; Peter David Davis, Oxford; David Festus Charles Moffat, Berkshire, all of (GB)

(73) Assignee: Celltech Therapeutics Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/420,732

(22) Filed: Oct. 20, 1999

Related U.S. Application Data

(63) Continuation of application No. 09/042,402, filed on Mar. 13, 1998, now Pat. No. 6,048,866.

(30) Foreign Application Priority Data

Mar. 14, 1997 (GB) .............................................. 9705361

(51) Int. Cl.[7] ...................... A01N 43/54; A61K 31/505; C07D 239/02
(52) U.S. Cl. ....................... 514/272; 544/321
(58) Field of Search ........................ 544/321; 514/272

(56) References Cited

U.S. PATENT DOCUMENTS

| | | | |
|---|---|---|---|
| 3,947,467 A | 3/1976 | Verge et al. ............. | 260/310 R |
| 4,012,495 A | 3/1977 | Schmiechen et al. ........ | 514/424 |
| 4,015,017 A | 3/1977 | Gazave ....................... | 514/687 |
| 4,153,713 A | 5/1979 | Huth et al. .................. | 514/423 |
| 4,193,926 A | 3/1980 | Schmiechen et al. ........ | 548/517 |
| 4,303,649 A | 12/1981 | Jones ............................ | 514/8 |
| 4,548,940 A | 10/1985 | Ife .............................. | 514/272 |
| 4,694,009 A * | 9/1987 | Hubele et al. ............... | 514/269 |
| 4,788,195 A | 11/1988 | Torley et al. ............... | 514/252 |
| 4,792,561 A | 12/1988 | Walker et al. .............. | 514/312 |
| 4,876,252 A | 10/1989 | Torley et al. ............ | 514/224.8 |
| 4,897,396 A | 1/1990 | Hubele ....................... | 514/275 |

(List continued on next page.)

FOREIGN PATENT DOCUMENTS

| | | |
|---|---|---|
| DE | 250 1443 | 7/1975 |
| DE | 34 36 380 A1 | 4/1986 |
| EP | 0 233 461 A2 | 8/1987 |
| EP | 0 295 210 A1 | 12/1988 |
| EP | 0 337 943 A2 | 10/1989 |
| EP | 0 393 500 A1 | 10/1990 |
| EP | 0 490 823 A1 | 6/1991 |
| EP | 0 470 805 A1 | 2/1992 |
| EP | 0 497 564 A1 | 8/1992 |
| EP | 0 511 865 A1 | 11/1992 |
| EP | 0 537 742 A2 | 4/1993 |
| EP | 0 564 409 A1 | 10/1993 |

(List continued on next page.)

OTHER PUBLICATIONS

Nanjo et al., "Preparation of 2–anilinopyramidines as agricultural fungicides", Chemical Abstract, vol. 116: 209703 (1992).*
Kroon, A.P. et al., "SN(ANRORC) [addition nucleophillic ring opening–ring closing]–mechanism. XIII. SN(ANRORC) mechanism in the amination of 2–substituted 4–phenylpyrimidines with potassijm amide in liquid ammonia," Recl. Trav. Chim. Pays–Bas, 1974, 93(12), 325–328, Chemical Abstract No. 83:43256.
Kroon, A.P., et al., "On the occurence of an $S_N$(ANRORC) mechanism in the amination of 2–substituted 4–phenylpyrmidines with potassium amide in liquid ammonia," J. Royal Netherlands Chem. Soc., 1974, 93/12, 325–328.
Ames, D.E. et al., "Some Dipyridylalkanes", J. Chem. Soc., 1962, 1475–1481.
Ashton, "Selective Type IV Phosphodiesterase Inhibitors as Antiasthmatic Agents. The Syntheses and Biological Activities of 3–(Cyclopentyloxy)–4–methyoxybenzamides and Analogues", J. Med. Chem., 1994, 37, 1696–1703.
Barton, D. et al., "A useful synthesis of pyrroles from nitroolefins", Tetrahedron, 1990, 46(21), 7587–7598 (HCAPLUS 1991:163917, 2 pages).
Beavo & Reifsnyder, "Primary Sequence of Cyclic Nucleotide Phosphodiesterase Isozymes and the Design of Selective Inhibitors" TIPS, 1990, 11, 150–155.
Buu–Hoi, N.P. et al., "Bromination of Some 1,2,2–Triarlethylenes" J. of Organic Chemistry, 1958, 1261–1263.

(List continued on next page.)

Primary Examiner—Mukund J. Shah
Assistant Examiner—Tamthom N. Truong
(74) Attorney, Agent, or Firm—Woodcock Washburn Kurtz Mackiewicz & Norris LLP

(57) ABSTRACT

Compounds of formula (1) are described:

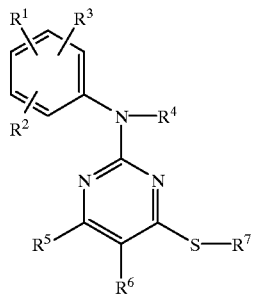

(1)

and the salts, solvates, hydrates and N-oxides thereof, in which $R^1$, $R^2$, $R^3$, $R^4$, $R^5$, $R^6$ and $R^7$ have the meanings given in claim 1. The compounds are selective inhibitors of protein kinases, especially src-family protein kinases and are of use in the prophylaxis and treatment of immune diseases, hyperproliferative disorders and other diseases in which inappropriate protein kinase action is believed to have a role.

20 Claims, No Drawings

U.S. PATENT DOCUMENTS

| | | | |
|---|---|---|---|
| 4,921,862 A | 5/1990 | Walker et al. | 514/312 |
| 4,966,622 A * | 10/1990 | Rempfler et al. | 71/92 |
| 4,971,959 A | 11/1990 | Hawkins | 514/150 |
| 4,973,690 A | 11/1990 | Rempfler et al. | 544/279 |
| 4,987,132 A | 1/1991 | Mase et al. | 514/252 |
| 5,124,455 A | 6/1992 | Lombardo | 546/181 |
| 5,128,358 A | 7/1992 | Saccomano et al. | 514/392 |
| 5,159,078 A | 10/1992 | Rempfler et al. | 544/330 |
| 5,164,372 A | 11/1992 | Matsuo et al. | 514/19 |
| 5,175,167 A | 12/1992 | Zipperer et al. | 514/277 |
| 5,177,085 A | 1/1993 | Naef | 514/307 |
| 5,236,918 A | 8/1993 | Amschler et al. | 514/247 |
| 5,274,002 A | 12/1993 | Hawkins | 514/530 |
| 5,298,511 A | 3/1994 | Waterson | 514/311 |
| 5,326,898 A | 7/1994 | Chandraratna | 560/17 |
| 5,340,827 A | 8/1994 | Beeley et al. | 514/352 |
| 5,491,147 A | 2/1996 | Boyd et al. | 514/247 |
| 5,521,184 A | 5/1996 | Zimmermann | 514/252 |
| 5,550,137 A | 8/1996 | Beeley et al. | 514/354 |
| 5,580,888 A | 12/1996 | Warrellow et al. | 514/332 |
| 5,593,997 A | 1/1997 | Dow et al. | 514/258 |
| 5,608,070 A | 3/1997 | Alexander et al. | 546/270 |
| 5,622,977 A | 4/1997 | Warrellow et al. | 514/336 |
| 5,633,257 A | 5/1997 | Warrellow et al. | 514/277 |
| 5,674,880 A | 10/1997 | Boyd et al. | 514/307 |
| 5,691,376 A | 11/1997 | Caggiano et al. | 514/532 |
| 5,693,659 A | 12/1997 | Head et al. | 514/357 |
| 5,698,711 A | 12/1997 | Palfreyman | 549/66 |
| 5,716,967 A | 2/1998 | Kleinman | 514/313 |
| 5,723,460 A | 3/1998 | Warrellow et al. | 514/247 |
| 5,728,708 A | 3/1998 | Zimmerman | 514/275 |
| 5,739,144 A | 4/1998 | Warrellow et al. | 514/277 |
| 5,753,663 A | 5/1998 | Flippin et al. | 514/257 |
| 5,776,958 A | 7/1998 | Warrellow et al. | 514/345 |
| 5,780,477 A | 7/1998 | Head et al. | 514/277 |
| 5,780,478 A | 7/1998 | Alexander et al. | 514/277 |
| 5,786,354 A | 7/1998 | Warrellow et al. | 514/277 |
| 5,798,373 A | 8/1998 | Warrellow et al. | 514/357 |
| 5,849,770 A | 12/1998 | Head et al. | 514/357 |
| 5,851,784 A | 12/1998 | Owens et al. | 435/19 |
| 5,859,034 A | 1/1999 | Warrellow et al. | 514/357 |
| 5,866,593 A | 2/1999 | Warrellow et al. | 514/336 |
| 5,891,896 A | 4/1999 | Warrellow et al. | 514/357 |
| 5,922,741 A | 7/1999 | Davis et al. | 514/341 |
| 6,080,790 A | 6/2000 | Boyd et al. | 514/650 |
| 6,093,716 A | 7/2000 | Davis et al. | 514/253 |
| 6,096,747 A | 8/2000 | Beeley et al. | 514/256 |

FOREIGN PATENT DOCUMENTS

| | | |
|---|---|---|
| FR | 1 285 932 | 8/1972 |
| FR | 2 313 422 | 12/1976 |
| FR | 2 545 356 A1 | 11/1984 |
| GB | 1588639 | 4/1981 |
| JP | 90-113923 * | 4/1990 |
| JP | 3-77872 | 4/1991 |
| JP | 3-77923 | 4/1991 |
| WO | WO 87/06576 | 11/1987 |
| WO | WO 91/15451 | 10/1991 |
| WO | WO 91/16892 | 11/1991 |
| WO | WO 92/00968 | 1/1992 |
| WO | WO 92/06085 | 4/1992 |
| WO | WO 92/06963 | 4/1992 |
| WO | WO 95/09852 | 4/1992 |
| WO | WO 92/07567 | 5/1992 |
| WO | WO 92/12961 | 8/1992 |
| WO | WO 92/19594 | 11/1992 |
| WO | WO 92/19602 | 11/1992 |
| WO | WO 93/10118 | 5/1993 |
| WO | WO 93/19748 | 10/1993 |
| WO | WO 94/02465 | 2/1994 |
| WO | WO 94/10118 | 5/1994 |
| WO | WO 94/12461 | 6/1994 |
| WO | WO 94/13661 | 6/1994 |
| WO | WO 94/14742 | 7/1994 |
| WO | WO 94/20446 | 9/1994 |
| WO | WO 94/20455 | 9/1994 |
| WO | WO 95/04046 | 2/1995 |
| WO | WO 95/09847 | 4/1995 |
| WO | WO 95/09851 | 4/1995 |
| WO | WO 95/09853 | 4/1995 |
| WO | WO 95/17386 | 6/1995 |
| WO | WO 95/31451 | 11/1995 |
| WO | WO 95/33727 | 12/1995 |
| WO | WO 95/35281 | 12/1995 |
| WO | WO 95/35283 | 12/1995 |
| WO | WO 96/14843 | 5/1996 |
| WO | WO 97/09297 | 3/1997 |
| WO | WO 97/09325 | 3/1997 |
| WO | WO 98/28281 | 7/1998 |
| WO | WO 98/58926 | 12/1998 |

OTHER PUBLICATIONS

Buu–Hoi et al., "New Method for the Synthesis of $\omega,\omega$–Diarylacetophenones Aminated in the Aromatic Nucleus. Plynitration of Triarlethylenes", Chem. Abstr., 1964, 61(13), 16006h.

Bortolus et al., "cis–trans Isomerization of azastilbenes photosensitized by biacetyl", Mol. Photochem., 1970, 2(4), 311–321, CAPLUS accession No. 1971–434722, 2 pages.

Chan, A.C. et al., "The Role of Protein Tyrosine Kinases and Protein Tyrosine Phosphatases in T Cell Antigen Receptor Signal Transduction", Annu. Rev. Immunol., 1994, 12, 555–592.

Chatterjee, A. et al., "Total Synthesis of Ring–C Aromatic 18–Nor Steroid", Tetrahedron, 1980, 36, 2513–2519.

Chemical Abstracts, "Hypoglycemic Pharmaceuticals Containing Manzammide Derivatives", Chem. Abstr., 1983, 99(6), No. 43558Z.

Chemical Abstracts, Registry No. 2732–15–2, prior to 1967, 1 page.

Chemical Abstracts, Registry No. 4593–13–9, prior to 1967, 1 page.

Clayton, S.E. et al., "Direct Aromatic tert–Butylation during the Synthesis of Thiochroman–4–ones", Tetrahedron, 1993, 49(4), 939–946.

Collins, R.F. et al., "The Chemotherapy of Schistosomiasis. Part IV. Some Ethers of 4–Amino–2–methoxyphenol", J. Chem. Soc., 1961, 1863–1879.

Daves, G.D. et al., "Pyrimidines. XIII. 2–and 6–Substituted 4–Pyrimidinecarboxylic Acids", J. Hev. Chem., 1964, 1 , 130–133.

Degani, I. et al., "Cationi etero–aromatici Nota VI—Sintesi di alcuni derivati del perclorato di tiacromilio", Boll. Sci. Fac. Chim. Ind. Bologna, 1966, 24(2–3), 75–91 (English Summary Only).

Dietl, F. et al., "Chinone von Benzo–und Dibenzokronenethern", Synthesis, 1985, 626–631.

Dent et al., "Inhibition of eosinophil cyclic nucleotide PDE activity and opsonised zymosan–stimulated respiratory burst by 'type IV'–selective PDE inhibitors", Br. J. Pharmacol., 1991, 103, 1339–1346.

El–Wakil et al., "Study of the proton magnetic resonance of methoxytamoxifen towards ortho–substitution", Chem. Abstr., 1992, 116, 255248t.

Fitzgerald, J.J. et al., "Reaction of benzocyclobutene oxides with nitriles: synthesis of hypecumine and other 3–substituted isooquinolines", *Tetrahedron Lett.*, 1994, 35(49), 9191–9194 (HCAPLUS 1995:272292, 2 pages).

Geissler, J.F. et al., "Thiazolidine–Diones. Biochemical and Biological Activity of a Novel Class of Tyrosine Protein Kinase Inhibitors", *J. Biol. Chem.*, 1990, 265(36), 22255–22261.

Green and Wuts, "Protective Group in Organic Synthesis", John Wiley & Sons, New York, 1991.

Griffin, R.W. et al., "1–Methyl–7–halo–2–naphthalenecarboxylic Acid Derivatives", *J. Organic Chem.*, 1964, 29(8), 2109–2116.

Gupta, A.S. et al., "Friedel–Crafts Condensation of Ethyl Allylmalonate with Anisole", *Tetrahedron*, 1967, 23, 2481–2490.

Hanks, S.K. et al., "The eukaryotic protein kinase superfamily: kinase (catalytic) domain structure and classification", *FASEB J.*, 1995, 9, 576–596.

Hanna, M.M. et al., "Syntheis and antimicrobial activity of some substituted 3–aryl–5–benzylidene–2–phenyl–4–imidazolone derivatives", *Bull. Fac. Pharm.*, 1994, 32(3), 353–359 (HCAPLUS 1996:586501, 2 pages).

Hart et al., "Alkylation of Phenol with a Homoallylic Halide", *J. Am. Chem. Soc.*, 1963, 85, 3269–3273.

Heaslip et al., "Phosphodiesterase–IV Inhibition, Respiratory Muscle Relaxation and Bronchodilation by WAY–PDA–641", *J. Pharm. Exper. Ther.*, 1993, 268(2), 888–896.

Hirose et al., "Styrene Derivatives and Electrophotpgraphic Photoreceptor Containing Them", *Chem. Abstr.*, 1993, 118, 136183z.

Ife, R.J., "Aminopyrimidinone derivatives as histamine H1–antagonists", CAPLUS Abstract No. 101:211163, Registry No. 92993–05–0, Jul. 4, 1984, 2 pages.

Ishikura, M. et al., "An Efficient Synthesis of 3–Heteroarylpyridines via Diethyl–(3–pyridyl)–borane" *Synthesis*, 1984, 936–938.

Iwashita, S. et al., "Signal Transduction System for Growth Factor Receptors Associated with Tyrosine Kinase Activity: Epidermal Growth Factor Receptor Singalling and its Regulation", *Cellular Signalling*, 1992, 4(2), 123–132.

Johnson et al., "Identification of Retinoic Acid Receptor β Subtype Specific Agonists", *J. Med. Chem.*, 1996, 39(26), 5027–5030.

Kaiser et al., "Selective metalations of methylated pyridines and quinolines", *J. Org. Chem.*, 1973, 38(1), 71–75, CAPLUS accession No. 1973–71853, 2 pages.

Karlsson et al., "T–Lymphocyte and Inflammatory Cell Research in Asthma", Joller, G. et al. (eds.), Academic Press, 1993, 323–347.

Kefalas, P. et al., "Signalling by the $p60^{c-src}$ Family of Protein–Tyrosine Kinases", *Int. J. Biochem. Cell Biol.*, 1995, 27(6), 551–563.

Lehmann, J. et al., "Lactones; XIII. Grignard Reaction Followed by Phase–Transfer Oxidation: A Convenient Synthesis of γ,γ–Distributed γ–Butyrolactones from γ–Butyrolactone", *Synthesis*, 1987, 1064–1067 (English abstract only).

Lisle, H. et al., "IL–2–Induced Eosinophilia in the Rat Pleural Cavity: The Effect of Dexamethasone and Indomethacin", *Br. J. Pharmacol.* 1993, 108, 230.

Livi et al., "Cloning and Expression of cDNA for a Human Low–$K_m$3 Rolipram–sensitive Cyclic AMP Phosphodiesterase", *Molecular and Cellular Biol.* 1990, 10(6), 2678–2686.

Manhas et al., "heterocyclic Compounds XII. Quinazoline Derivatives as Potential Antifertility Agents(1)" *J. Heterocyclic Chem.*, 1979, 16, 711–715.

Mathison et al., "Synthesis and Hypotensive Properties of Tetrahydroixoquinolines", *J. Med. Chem.*, 1973, 16(4), 332–336.

Meyers, A.J. et al., "Oxazolines. XI. Synthesis of Fuctionalized Aromatic and Aliphatic Acids. A Useful Protecting Group for Carboxylic Acids Against Grignard and Hydride Reagents", *J. Org. Chem.* 1974, 39(18), 2787–2793.

Meyers, A.I. et al., "The Synthesis of 2–Pyridones from Cyclic Cyano Ketones. A New Aromatization Procedure for Dihydro–2–pyridones", *J. Org. Chem.*, 1964, 29, 1435–1438.

Mezheritskaya, "Synthesis and properties of carboxonium het=erocyclic systems. VII. Synthesis and properties of 2–benzyl–substituted 1,3–dioxolanium salts", *Chem. Abstr.*, 1980, 93, 95160j, 635.

Mitsunobu, O., "The Use of Diethyl Azodicarboxylate and Triphenylphosphine in Synthesis and Transformation of Natural Products" *Synthesis*, 1981, 1–28.

Miyaura, N. et al., "The Palladium–Catalyzed Cross–Coupling Reaction of Phenylboronic Acid with Haloarenes in the Presence of Bases", *Synth. Comm.*, 1981, 11, 513–519.

Nanjo et al., "Preparation of 2–anilinopyrimidines as agricultural fungicides", *Chem. Abstr.*, 1992, 116(21), No. 116:209703q.

Newton, A.C., "Protein Kinase C: Structure, Function, Regulation", *J. Biol. Chem.*, 1995, 270(48), 28495–28498.

Nicholson et al., "Differential Modulation of Tissue Function and Therapeutic Potential of Selective Inhibitors of Cyclic Nucleotide Phosphodiesterase Isoenzymes" *TIPS*, 1991, 12, 19–27.

O'Connor et al., "Voltammetry and Controlled Potential Oxidation of 3,4–dimethoxypropenylbenzene at a rotating platinum electrode in unbuffered acetonitrile and in acetonitrile–pyridine solution" *Chem. Abstr.*, 1964, 60(8) #10203.4.

Ohtani, Y. et al., "Studies on Pitch Problems Caused by Pulping and Bleaching of Tropical Woods. XIV. Chemistry of the Aurone Derivatives at the Conventional Bleaching Stages", *Acta Chem. Scand.*, 1982, 613–621.

Pickett, W.C. et al., "Modulation of Eicosanoid Biosynthesis by Novel Pyridinylpyrimidines", *Ann. N.Y. Acad. Sci.*, 1994, 744, 299–305.

Pines, J., "Cyclins and cyclin–dependent kinases: take your partners", *TIBS*, 1993, 18, 195–197.

Plé, N. et al., "Metalation of Diazines. XI. Directed Ortho–Lithiation of Fluoropyrimidines and Applictaion to Synthesis of an Azacarboline", *J. Heterocyclic Chem.*, 1994, 31, 1311–1315.

Porter et al., "Preparation of 6–phenyl–3–(5–tetrazolyl)pyridin–=2(H)–one Derivatives as Cyclic AMP–dependent Protein Kinase Agonists" *Chem. Abstr.*, 1992, 117(9), 90296n.

Ramalingam et al., "Synthesis and Pharmacology of2, 5–Disubstituted 1,3,4–Zxadiazoles" *J. Indian Chem. Soc.*, 1981, 58(3), 269–271.

Reddy et al., "Inhibition of Breast Cancer Cell Growth in Vitro by a Tyrosine Kinase Inhibitor" *Cancer Research*, 1992, 52, 3636–3641.

Sakakibara, K. et al., "Preparation of N–pyridyl–4–(benzyloxy)benzamides as Cardiotonics", *Chem. Abstr.*, 1988, 108, No. 131583p.

Sánchez, H.I. et al., "Formal Total Synthesis of β–Pipitzol", *Tetrahedron*, 1985, 41(12), 2355–2359.

Schneider et al., "Catechol Estrogens of the 1,1, 2–Triphenylbut–1–ene Type: Relationship Between Structure, Estradiol Receptor Affinity, Estrogenic and Antiestrogenic Properties, and Mammary Tumor Inhibiting Activities" *J. Med. Chem.*, 1986, 29, 1355–1362.

Seitz et al., "Fluorotamoxifen. A Caveat on the Generality of Electrophilic Destannylation" *Chem. Abstr.*, 1989, 111, 57133k.

Sharp, M.J. et al., "Synthetic Connections to the Aromatic Directed Metalation Reaction. Functionalized Aryl Boronic Acids by Ipso Borodesilylation; General Synthesis of Unsymmetrical iphenyls and n–Terphenyls", *Tetrahedron Lett.*, 1987, 28(43), 5093–5096.

Shioiri et al., "New Methods and Reagents in Organic Synthesis. 3. Diethyl Phosphorocyanidate: A New Reagent for C–Acylation", *J. Org. Chem.*, 1978, *43*, 3631–3632.

Spada, A.P. et al., "Small Molecule Inhibitors of Tyrosine Kinase Activity", *Exp. Opin. Ther. Patents*, 1995, 5(8), 805–817.

Takeuchi, I. et al., "On the Antimocrobial Activity and Syntheses of Carbanilide and Salicylanilide Derivatives", *Chem. Abstr.*, 1983, 98, No. 125577y.

Thompson, W.J. and Gaudino, J., "A General Synthesis of 5–Arylnicotinates" *J. Org. Chem.*, 1984, 49, 5237–5243.

Tollari, S. et al., "Intramolecular amination of olefins. Synthesis of 2–substituted–4–quinolones from 2–nitrochalcones catalyzed by ruthenium", *J. Chem. Soc.*, 1994, 15, 1741–1742 (HCAPLUS 1994:605194, 2 pages).

Tominaga et al., "Polarized Ethylenes. IV. Synthesis of Polarized Ethylenes Using Thioamides and Methyl Dithiocarboxylates and Their Application to Syntheses of Pyrazoles, Pyrimidines, Pyrazolo[3,4-d ]pyrimidines, and 5–Aza [2.2.3]cyclazines", *J. Het. Chem.*, 1990, 27, 647–660.

Trost and Fleming (eds.), *Comprehensive Organic Synthesis*, Pergamon Press, New York, 1991, 3, 531–541.

Tsutsumi, K. et al., "Preparation of (Dialkoxyphosphinoylmethyl) benzamides as Antihyperlipidemics", *Chem. Abstr.*, 1990, 113, No. 6599a.

Vida et al., "Electrophilic Amination: Preparation and Use of N–Boc–3–(–4–cyanophenyl)oxaziridine, a New Reagent That Transfers a N– Boc Group to N–t0 and C–Nucleophiles", *J. Org. Chem.*, 1993, 58, 4791–4793.

Yamaguchi, H., "Guanidinobenzene derivatives as anticoagulants ", *Chem. Absts.*, 1989, 110, 655 (Abstract No. 94706z).

Yamato, M. et al., "Chemical structure and sweet taste of isocoumarin and related compounds. VI", *Chem. Pharm. Bull.*, 1975, 23(12), 3101–3105 (HCAPLUS 1976:99154, 2 pages).

Yeadon et al., "Mechanisms Contributing to Ozone–Induced Bronchial Hyperreactivity in Guinea Pigs ", *Pulmonary Pharm.*, 1992, 5, 39–50.

Yoneda et al., "The Antiproliferative Effects of Tyrosine Kinase Inhibitors Tyrphostins on a Human Squamous Cell Carcinoma in Vitro and in Nude Mice " *Cancer Research*, 1991, 51, 4430–4435.

Zimmermann, J. et al., "Phenylamino–Pyrimidine (PAP) Derivatives: A New Class of Potent and Selective Inhibitors of Protein Kinase C (PKC)", *Arch. Pharm.*, 1996, 329(7), 371–376.

Zimmermann, J. et al., "Phenylamino–Pyrimidine (PAP)— Derivatives: A New Class of Potent and Highly Selective PDGF–Receptor Autophosphorylation Inhibitors", *Bioorg. Med. Chem. Lett.*, 1996, 6(11), 1221–1226.

Zimmermann, J. et al., "Potent and Selective Inhbitors of the ABL–Kinase Phenlyamino–Pyrimidine (PAP) Derivatives", *Bioorg. Med. Chem. Lett.*, 1997, 7(2), 187–192

\* cited by examiner

SUBSTITUTED 2-ANILINOPYRIMIDINES USEFUL AS PROTEIN KINASE INHIBITORS

CROSS-REFERENCE TO RELATED APPLICATION

This application is a continuation of U.S. application Ser. No. 09/042,402, filed Mar. 13, 1998, now U.S. Pat. No. 6,048,866.

This invention relates to substituted 2-anilinopyrimidines, to processes for their preparation, to pharmaceutical compositions containing them, and to their use in medicine.

Protein kinases participate in the signalling events which control the activation, growth and differentiation of cells in response to extracellular mediators and to changes in the environment. In general, these kinases fall into two groups; those which preferentially phosphorylate serine and/or threonine residues and those which preferentially phosphorylate tyrosine residues [Hanks, S K, Hunter T, FASEB. J. 9, 576–596 (1995)]. The serine/threonine kinases include for example, protein kinase C isoforms [Newton A C, J. Biol. Chem. 270, 28495–28498 (1995)] and a group of cyclin-dependent kinases such as cdc2 [Pines J, Trends in Biochemical Sciences 18, 195–197 (1995)]. The tyrosine kinases include membrane-spanning growth factor receptors such as the epidermal growth factor receptor [Iwashita S and Kobayashi M. Cellular Signalling 4, 123–132 (1992)], and cytosolic non-receptor kinases such as ZAP-70 and csk kinases [Chan C et al Ann. Rev. Immunol. 12, 555–592 (1994)]. A particular group of non-receptor tyrosine kinases are a group known as the src family which includes $p56^{lck}$ and $p59^{fyn}$ [Kefelas P et al International Journal of Biochemistry and Cell Biology 27, 551–563 (1995)].

Inappropriately high protein kinase activity has been implicated in many diseases resulting from abnormal cellular function. This might arise either directly or indirectly, for example by failure of the proper control mechanisms for the kinase, related for example to mutation, over-expression or inappropriate activation of the enzyme; or by over- or underproduction of cytokines or growth factors also participating in the transduction of signal upstream or downstream of the kinase. In all of these instances, selective inhibition of the action of the kinase might be expected to have a beneficial effect.

We have now found a series of substituted 2-anilinopyrimidines which are potent and selective inhibitors of protein kinases, especially src-family protein kinases. The compounds are thus of use in the prophylaxis and treatment of immune diseases, hyperproliferative disorders and other diseases in which inappropriate protein kinase action is believed to have a role.

Thus, according to one aspect of the invention, we provide a compound of formula (1):

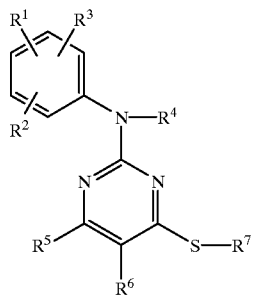

wherein $R^1$ is a —$XR^8$ group [where X is a covalent bond, —O—, —S—, —C(O)—, —C(S)—, —C(O)O—, —S(O)—, —S(O$_2$)—, —CH$_2$—, -or N($R^9$)— [where $R^9$ is a hydrogen atom or a straight or branched alkyl group] and $R^8$ is a hydrogen atom or an optionally substituted aliphatic, cycloaliphatic, heteroaliphatic, heterocycloaliphatic, aromatic or heteroaromatic group], or a —NO$_2$, —CN, —SO$_2$NH$_2$, —SO$_2$NHR$^8$, —SO$_2$N($R^8$)$_2$ [where each $R^8$ group may be the same or different], —CONH$_2$, —CONHR$^8$, —CON($R^8$)$_2$ [where each $R^8$ group may be the same or different], —CSNH$_2$, —CSNHR$^8$, —CSN($R^8$)$_2$ [where each $R^8$ group may be the same or different], —NH$_2$ or substituted amino group;

$R^2$ and $R^3$ which may be the same or different is each a hydrogen or halogen atom or a group selected from an optionally substituted aliphatic, cycloaliphatic, heteroaliphatic, heterocycloaliphatic, —OH, —OR$^{10}$ [where $R^{10}$ is an optionally substituted aliphatic group], —OR$^{10a}$ [where $R^{10a}$ is an optionally substituted cycloaliphatic, heteroaliphatic, heterocycloaliphatic, aromatic or heteroaromatic group] —SH, —NO$_2$, —CN, —SR$^8$, —COR$^8$, S(O)R$^8$, —SO$_2$R$^8$, —SO$_2$NH$_2$, —SO$_2$NHR$^8$, —SO$_2$N($R^8$)$_2$ [where each $R^8$ group may be the same or different] —CO$_2$H, —CO$_2$R$^8$, —CONH$_2$, —CONHR$^8$, —CON($R^8$)$_2$, [where each $R^8$ group may be the same or different] —CSNH$_2$, —CSNHR$^8$, —CSN($R^8$)$_2$, [where each $R^8$ group may be the same or different] —NH$_2$ or substituted amino group provided that when one or both of $R^2$ and $R^3$ is an —OR$^{10}$ group then $R^1$ is an —OR$^8$ group in which $R^8$ is an optionally substituted cycloaliphatic, heteroaliphatic, heterocycloaliphatic, aromatic or heteroaromatic group or an aliphatic group substituted by a cyclic amino group;

$R^4$ is a hydrogen atom or a straight or branched alkyl group;

$R^5$ is a hydrogen atom or an optionally substituted straight or branched alkyl, alkenyl or alkynyl group;

$R^6$ is a hydrogen or halogen atom or an amino, substituted amino, nitro, —CO$_2$H, or —CO$_2$R$^8$ group or a group —$X^1$—$R^{6a}$ where $X^1$ is a direct bond or a linker atom or group and $R^{6a}$ is an optionally substituted straight or branched alkyl, alkenyl or alkynyl group;

$R^7$ is an optionally substituted aliphatic, cycloaliphatic, heteroaliphatic, heterocycloaliphatic, aromatic or heteroaromatic group; and the salts, solvates, hydrates and N-oxides thereof.

When in the compounds of formula (1) $X^1$ is present as a linker atom or group it may be for example an —O— or —S— atom or a —C(O)—, —C(S)—, —S(O)—, —S(O)

$_2$—, —N(R$^{11}$)— [where R$^{11}$ is a hydrogen atom or a C$_{1-6}$ alkyl, e.g. methyl or ethyl, group], —CON(R$^{11}$)—, —OC(O)N(R$^{11}$)—, —CSN(R$^{11}$)—, —N(R$^{11}$)CO—, —N(R$^{11}$)C(O)O—, —N(R$^{11}$)CS—, —SON(R$^{11}$), —SO$_2$N(R$^{11}$), —N(R$^{11}$)SO$_2$—, —N(R$^{11}$)CON(R$^{11}$), —N(R$^{11}$)CSN(R$^{11}$), —N(R$^{11}$)SON(R$^{11}$)— or —N(R$^{11}$)SO$_2$N(R$^{11}$) group.

In the compounds of formula (1), when R$^1$ is —XR$^8$ and R$^8$ is an optionally substituted aliphatic group, R$^8$ may be an optionally substituted C$_{1-10}$ aliphatic group for example an optionally substituted straight or branched chain C$_{1-6}$ alkyl, e.g. C$_{1-3}$ alkyl, C$_{2-6}$ alkenyl, e.g. C$_{2-4}$ alkenyl, or C$_{2-6}$alkynyl, e.g. C$_{2-4}$ alkynyl group. Each of said groups may be optionally interrupted by one or two heteroatoms or heteroatom-containing groups represented by X$^2$ [where X$^2$ is an atom or group as just described for X$^1$], to form an optionally substituted R$^8$ heteroaliphatic group.

Particular examples of aliphatic groups represented by R$^8$ include optionally substituted —CH$_3$, —CH$_2$CH$_3$, —(CH$_2$)$_2$CH$_3$, —CH(CH$_3$)$_2$, —(CH$_2$)$_3$CH$_3$, —CH(CH$_3$)CH$_2$CH$_3$, —CH$_2$CH(CH$_3$)$_2$, —C(CH$_3$)$_3$, —(CH$_2$)$_4$CH$_3$, —(CH$_2$)$_5$CH$_3$, —CHCH$_2$, —CHCHCH$_3$, —CH$_2$CHCH$_2$, —CHCHCH$_2$CH$_3$, —CH$_2$CHCHCH$_3$, —(CH$_2$)$_2$CHCH$_2$, —CCH, —CCCH$_3$, —CH$_2$CCH, —CCCH$_2$CH$_3$, —CH$_2$CCCH$_3$, or —(CH$_2$)$_2$CCH groups. Where appropriate each of said groups may be optionally interrupted by one or two atoms and/or groups X$^2$ to form an optionally substituted heteroaliphatic group. Particular examples include —CH$_2$X$^2$CH$_3$, —CH$_2$X$^2$CH$_2$CH$_3$, —(CH$_2$)$_2$X$^2$CH$_3$ and —(CH$_2$)$_2$X$^2$CH$_2$CH$_3$ groups.

The optional substituents which may be present on these aliphatic and/or heteroaliphatic groups include one, two, three or more substituents selected from halogen atoms, e.g. fluorine, chlorine, bromine or iodine atoms, or hydroxyl, C$_{1-6}$ alkoxy, e.g. methoxy or ethoxy, thiol, C$_{1-6}$ alkylthio e.g. methylthio or ethylthio, —SC(NH)NH$_2$, —CH$_2$C(NH)NH$_2$, amino, substituted amino or cyclic amino groups.

Substituted amino groups include for example groups of formulae —NR$^9$R$^{10}$ [where R$^9$ is an optionally substituted C$_{1-6}$ alkyl, C$_{2-6}$alkenyl or C$_{2-6}$alkynyl group optionally interrupted by one or two heteroatoms or heteroatom-containing groups represented by X$^3$ (where X$^3$ is an atom or group as described above for X$^1$) and R$^{10}$ is a hydrogen atom or is a group as just defined for R$^9$], —N(R$^{10}$)COR$^9$, —N(R$^{10}$)CSR$^9$, —N(R$^{10}$)SOR$^9$, —N(R$^{10}$)SO$_2$R$^9$, —N(R$^{10}$)CONH$_2$, —N(R$^{10}$)CONR$^9$R$^{10}$, —N(R$^{10}$)C(O)OR$^9$, —N(R$^{10}$)C(NH)NH$_2$, N(R$^{10}$)C(NH)NR$^9$R$^{10}$, —N(R$^{10}$)CSNH$_2$, —N(R$^{10}$)CSNR$^9$R$^{10}$, —N(R$^{10}$)SONH$_2$, —N(R$^{10}$)SONR$^9$R$^{10}$, —N(R$^{10}$)SONH$_2$, —N(R$^{10}$)SO$_2$NH$_2$, N(R$^{10}$)SO$_2$NR$^9$R$^{10}$, or —N(R$^{10}$)Cyc$^1$ [where Cyc$^1$ is an optionally substituted C$_{3-7}$ monocyclic carbocyclic group optionally containing one or more —O— or —S— atoms or —N(R$^{11}$)—, —C(O)—, —C(S)—, —S(O)— or —S(O$_2$)— groups].

Cyclic amino substituents which may be present on R$^8$ aliphatic or heteroaliphatic groups include groups of formula —NHet$^1$, where —NHet$^1$ is an optionally substituted C$_{3-7}$cyclic amino group optionally containing one or more other heteroatoms or heteroatom containing groups selected from —O— or —S— atoms —N(R$^{11}$)—, —C(O), —C(S)—, —S(O)— or —S(O$_2$)— groups.

Particular examples of amino, substituted amino and cyclic amino groups include —NH$_2$, methylamino, ethylamino, dimethylamino, diethylamino, —NHCyc$^1$ where Cyc$^1$ is an optionally substituted cyclopentyl, cyclohexyl, pyrrolidinyl, imidazolidinyl, pyrazolidinyl, piperidinyl, morpholinyl, piperazinyl or thiomorpholinyl group, or —NHet$^1$ where —NHet$^1$ is an optionally substituted pyrrolidinyl, imidazolidinyl, pyrazolidinyl, piperidinyl, morpholinyl, piperazinyl or thiomorpholinyl group. Optional substituents which may be present on these groups and substituted and cyclic amino groups in general include one, two or three halogen atoms, e.g. fluorine, chlorine, bromine or iodine atoms, or C$_{1-4}$alkyl, e.g. methyl or ethyl, hydroxyl, or C$_{1-4}$alkoxy, e.g. methoxy or ethoxy groups.

When R$^8$ is present in compounds of formula (1) as an optionally substituted cycloaliphatic group it may be an optionally substituted C$_{3-10}$cycloaliphatic group. Particular examples include optionally substituted C$_{3-10}$cycloalkyl, e.g. C$_{3-7}$cycloalkyl, or C$_{3-10}$cycloalkenyl e.g. C$_{3-7}$cycloalkenyl groups.

Heteroaliphatic or heterocycloaliphatic groups represented by R$^8$ include the aliphatic or cycloaliphatic groups just described for R$^8$ but with each group additionally containing one, two, three or four heteroatoms or heteroatom-containing groups represented by X$^2$, where X$^2$ is as described above.

Particular examples of R$^8$ cycloaliphatic and heterocycloaliphatic groups include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, 2,4-cyclopentadien-1-yl, 3,5,-cyclohexadien-1-yl, tetrahydrofuranyl, pyrroline, e.g. 2- or 3-pyrrolinyl, pyrrolidinyl, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, piperidinyl, 1,4-dioxanyl, morpholinyl, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, oxathiazinyl, e.g. 1,2,5 or 1,2,6-oxathiazinyl, or 1,3,5-oxadiazinyl groups.

Optional substituents which may be present on R$^8$ cycloaliphatic and heterocycloaliphatic groups include those optional substituents described above for R$^8$ when it is an aliphatic group. The heterocycloaliphatic groups may be attached to the remainder of the molecule of formula (1) through any appropriate ring carbon or heteroatom.

When R$^8$ is present as an aromatic group in compounds of formula (1) it may be for example an optionally substituted monocyclic or bicyclic fused ring C$_{6-12}$ aromatic group, such as an optionally substituted phenyl, 1- or 2-naphthyl, 1- or 2-tetrahydronaphthyl, indanyl or indenyl group.

Heteroaromatic groups represented by R$^8$ include optionally substituted C$_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example live- or six-membered heteroaromatic groups containing one, two, three or four heteroatoms selected from oxygen, sulphur or nitrogen atoms. Bicyclic heteroaromatic groups include for example nine- to thirteen-membered fused-ring heteroaromatic groups containing one, two or more heteroatoms selected from oxygen, sulphur or nitrogen atoms.

Examples of heteroaromatic groups represented by R$^8$ include optionally substituted pyrrolyl, furyl, thienyl, imidazolyl, N-methylimidazolyl, N-ethyl-imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydrobenzofuryl, isobenzofuryl, benzothienyl, benzotriazolyl, isobenzothienyl, indolyl, isoindolyl, benzimidazolyl imidazo[1,2-a]pyridyl, benzothiazolyl, benzoxazolyl, benzopyranyl, [3,4-dihydro]benzopyranyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Optional substituents which may be present on any of the above aromatic or heteroaromatic groups in compounds of formula (1) include one, two, three or more substituents, each represented by the group $R^{12}$. The substituent $R^{12}$ may be selected from an atom or group $R^{13}$ or —Alk$(R^{13})_m$, where $R^{13}$ is a halogen atom, or an amino (—NH$_2$), —NHR$^{14}$ [where $R^{14}$ is an —Alk$(R^{13})_m$, heterocycloalkyl, —Alk-heterocycloalkyl, aryl or heteroaryl group], —N$(R^{14})_2$ [where each $R^{14}$ group is the same or different], nitro, cyano, hydroxyl (—OH), —OR$^{14}$, formyl, carboxyl (—CO$_2$H), esterified carboxyl, thiol (—SH), —SR$^{14}$, —COR$^{14}$, —CSR$^{14}$, —SO$_3$H, —SO$_2$R$^{14}$, —SO$_2$NH$_2$, —SO$_2$NHR$^{14}$, SO$_2$N[R$^{14}$]$_2$, —CONH$_2$, —CSNH$_2$, —CONHR$^{14}$, —CSNHR$^{14}$, —CON[R$^{14}$]$_2$, —CSN[R$^{14}$]$_2$, —N$(R^{11})$SO$_2$H [where $R^{11}$ is as defined above], —N$(R^{11})$SO$_2$R$^{14}$, —N[SO$_2$R$^{14}$]$_2$, —N$(R^{11})$SO$_2$ NH$_2$, —N$(R^{11})$SO$_2$NHR$^{14}$, —N$(R^{11})$SO$_2$N[R$^{14}$]$_2$, —N$(R^{11})$COR$^{14}$, —N$(R^{11})$CONH$_2$, —N$(R^{11})$CONHR$^{14}$, —N$(R^{11})$CON[R$^{14}$]$_2$, —N$(R^{11})$CSR$^{14}$, —N$(R^{11})$CSNH$_2$, —N$(R^1)$CSNHR$^{14}$, —N$(R^{11})$CSN[R$^{14}$]$_2$, —N$(R^{11})$C(O)OR$^{14}$, or an optionally substituted cycloalkyl, aryl or heteroaryl group; Alk is a straight or branched $C_{1-6}$ alkylene, $C_{2-6}$ alkenylene or $C_{2-6}$ alkynylene chain, optionally interrupted by one, two or three —O— or —S— atoms or S—(O)—, —S(O)$_2$— or —N$(R^{11})$— groups; and m is zero or an integer 1, 2 or 3.

When in the group —Alk$(R^{13})_m$ m is an integer 1, 2 or 3, it is to be understood that the substituent or substituents $R^{13}$ may be present on any suitable carbon atom in —Alk. Where more than one $R^{13}$ substituent is present these may be the same or different and may be present on the same or different atom in —Alk or in $R^7$ as appropriate. Thus for example, $R^7$ may represent a —CH$(R^{13})_2$ group, such as a —CH(OH)Ar group where Ar is an aryl or heteroaryl group as defined below. Clearly, when m is zero and no substituent $R^{13}$ is present the alkylene, alkenylene or alkynylene chain represented by Alk becomes an alkyl, alkenyl or alkynyl group.

When $R^{13}$ is a halogen atom it may be for example a fluorine, chlorine, bromine, or iodine atom.

Esterified carboxyl groups represented by the group $R^{13}$ include groups of formula —CO$_2$Alk$^1$ wherein Alk$^1$ is a straight or branched, optionally substituted $C_{1-8}$ alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the Alk$^1$ group include $R^{13}$ substituents described above.

When Alk is present in or as a substituent $R^{12}$ it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N$(R^{11})$ groups.

Optionally substituted cycloalkyl groups represented by the group $R^{13}$ include optionally substituted $C_{5-7}$ cycloalkyl groups such as optionally substituted cyclopentyl or cyclohexyl groups.

Heterocycloalkyl groups represented by the group $R^{12}$ or $R^{14}$ include optionally substituted heteroC$_{3-6}$cycloalkyl groups containing one or two oxygen, sulphur or nitrogen atoms. Particular examples of such groups include optionally substituted azetidinyl pyrrolidinyl, piperidinyl, piperazinyl, homopiperazinyl, morpholinyl or thiomorpholinyl groups. The heterocycloalkyl group may be attached to the remainder of the molecule through any of its ring carbon atoms, or where present, ring nitrogen atom. Where the group $R^{12}$ is an —Alk-heterocycloalkyl group, Alk may be as defined above and the heterocycloalkyl portion may be as just defined, attached to Alk through any of its ring carbon atoms, or where present, ring nitrogen atom.

Optional substituents which may be present on $R^{12}$, $R^{13}$ or $R^{14}$ cycloalkyl or heterocycloalkyl groups include one or two $C_{1-6}$ alkyl, e.g. methyl or ethyl, hydroxyl (—OH) hydroxy$C_{1-6}$alkyl, e.g. hydroxymethyl or hydroxyethyl, or $C_{1-6}$ alkoxy, e.g. methoxy or ethoxy groups. The substituent (s) may be present on any available ring carbon or nitrogen atom as appropriate.

Aryl and heteroaryl groups represented by the groups $R^{13}$ or $R^{14}$ include for example optionally substituted monocyclic or bicyclic $C_{6-12}$ aromatic groups, or $C_{1-9}$ heteroaromatic groups such as those described above in relation to the group $R^8$.

Particularly useful atoms or groups represented by $R^{12}$ include fluorine, chlorine, bromine or iodine atoms, or $C_{1-6}$alkyl, $C_{1-6}$ alkylamino, $C_{1-6}$hydroxyalkyl, $C_{1-6}$alkylthiol, $C_{1-6}$alkoxy, hydroxy$C_{1-6}$alkoxy, amino$C_{1-6}$alkoxy, $C_{1-6}$alkylamino$C_{1-6}$alkoxy, $C_{1-6}$dialkylamino$C_{1-6}$akoxy, optionally substituted $C_{5-7}$cyclo-alkoxy, optionally substituted $C_{5-7}$cycloalkyl, optionally substituted $C_{5-7}$cycloalkylamino, halo$C_{1-6}$alkyl, halo$C_{1-6}$alkoxy, $C_{1-6}$alkylamino, amino (—NH$_2$), amino$C_{1-6}$alkyl, $C_{1-6}$dialkylamino, hydroxy$C_{1-6}$ alkylamino, amino$C_{1-6}$alkylamino, $C_{1-6}$alkylamino$C_{1-6}$alkylamino, $C_{1-6}$dialkylamino$C_{1-6}$alkylamino, $C_{1-6}$alkylamino$C_{1-6}$dialkylamino, $C_{1-6}$dialkylamino$C_{1-6}$dialkylamino, nitro, cyano, hydroxyl (—OH), formyl [HC(O)—], carboxyl (—CO$_2$H), —CH$_2$CO$_2$H, —OCH$_2$CO$_2$H, —CO$_2$Alk$^1$ [where Alk$^1$ is as defined above], —CH$_2$CO$_2$Alk$^1$, $C_{1-6}$alkoxycarbonyl$C_{1-6}$alkoxy, $C_{1-6}$ alkanoyl, optionally substituted phenyl$C_{1-6}$alkanoyl, thiol (—SH), thio$C_{1-6}$alkyl, —SC(NH)NH$_2$, sulphonyl (—SO$_3$H), $C_{1-6}$alkylsulphonyl, optionally substituted phenylsulphonyl, aminosulphonyl (—SO$_2$NH$_2$), $C_{1-6}$alkylaminosulphonyl, $C_{1-6}$dialkylaminosulphonyl, optionally substituted phenylamino-sulphonyl, carboxamido (—CONH$_2$), $C_{1-6}$alkyl-aminocarbonyl, $C_{1-6}$dialkylaminocarbonyl, optionally substituted phenyl-aminocarbonyl, aminocarbonylmethyl, $C_{1-6}$alkylaminocarbonylmethyl, optionally substituted benzylaminocarbonylmethyl, —NHC(S)NH$_2$, sulphonyl-amino (—NHSO$_2$H), $C_{1-6}$alkylsulphonylamino, $C_{1-6}$dialkylsulphonylamino, optionally substituted phenylsulphonylamino, aminosulphonylamino (—NHSO$_2$NH$_2$), $C_{1-6}$alkylaminosulphonylamino, $C_{1-6}$dialkylaminosulphonylamino, optionally substituted phenylaminosulphonylamino, aminocarbonyl-amino, $C_{1-6}$alkylaminocarbonylamino $C_{1-6}$dialkylaminocarbonylamino, phenylaminocarbonylamino, $C_{1-6}$alkanoylamino, amino$C_{1-6}$alkanoylamino, optionally substituted pyridylcarboxyamino, $C_{1-6}$alkanoylamino$C_{1-6}$alkyl, $C_{1-6}$alkoxycarbonylamino, optionally substituted heteroC$_{3-6}$cycloalkyl, piperidinyl, piperazinyl, 4-methylpiperazinyl, homopipeprazinyl, or morpholinyl, optionally substituted heteroC$_{3-6}$cycloalkylC$_{1-6}$alkyl, piperidinylC$_{1-6}$alkyl, piperazinylC$_{1-6}$alkyl or morpholinylC$_{1-6}$alkyl, optionally substituted heteroC$_{3-6}$alkylC$_{1-6}$alkylamino, optionally substituted heteroC$_{3-6}$cycloalkylamino, tetrazolyl, optionally substituted phenylamino, optionally substituted benzylamino, optionally substituted benzyloxy, or optionally substituted pyridiylmethylamino group.

Where desired, two $R^{12}$ substituents may be linked together to form a cyclic group such as a cyclic ether, e.g. a $C_{1-6}$alkylenedioxy group such as a methylenedioxy or ethylenedioxy group.

Especially useful $R^{12}$ substituents include for example fluorine, chlorine, bromine or iodine atoms, or a methylamino, ethylamino, hydroxymethyl, hydroxyethyl, methylthiol, ethylthiol, methoxy, ethoxy, n-propoxy, 2-hydroxyethoxy, 3-hydroxypropoxy, 4-hydroxybutoxy, 2-aminoethoxy, 3-aminopropoxy, 2-(methylamino)ethoxy, 2-(dimethylamino)ethoxy, 3-(dimethylamino)propoxy, cyclopentyloxy, cyclohexyl, cyclohexylamino, 2-hydroxycyclohexylamino, trifluoromethyl, trifluoromethoxy, methylamino, ethylamino, amino (—NH$_2$), aminomethyl, aminoethyl, dimethylamino, diethylamino, ethyl(methyl)amino, propyl(methyl)amino, 2-hydroxyethylamino, 3-hydroxypropylamino, 4-hydroxybutylamino, 2-aminoethylamino, 3-aminopropylamino, 4-aminobutylamino, 2-(methylamino)ethylamino, 2-(ethylamino)ethylamino, 2-(i-propylamino)ethylamino, 3-(i-propylamino)-propylamino, 2-(dimethylamino)ethylamino, 3-(dimethylamino)propylamino, 2-(diethylamino)ethylamino, 3-(diethylamino)propylamino, 2-(methylamino)-ethyl(methyl)amino, 3-(methylamino)propyl(methyl)amino, 2-(dimethyl-amino)ethyl(methyl)amino, 2-(dimethylamino)ethyl(ethyl)amino, nitro, cyano, hydroxyl (—OH), formyl [HC(O)—], carboxyl (—CO$_2$H), —CH$_2$CO$_2$H, —OCH$_2$CO$_2$H, —CO$_2$CH$_3$, —CO$_2$CH$_2$CH$_3$, —CH$_2$CO$_2$CH$_3$, —CH$_2$CO$_2$CH$_2$CH$_3$, —CH$_2$CO$_{2CH2}$phenyl, t-butoxycarbonylmethoxy, acetyl, phenacetyl, thio (—SH), thiomethyl, thioethyl, —SC(NH)NH$_2$, sulphonyl (—SO$_2$H), methylsulphonyl, methylaminosulphonyl, ethylaminosulphonyl, dimethylaminosulphonyl, diethylaminosulphonyl, carboxamido (—CONH$_2$), methylaminocarbonyl, ethylaminocarbonyl, dimethylaminocarbonyl, diethylaminocarbonyl, methylaminocarbonylmethyl, —NHC(S)NH$_2$, sulphonylamino (—NHSO$_2$H), methylsulphonylamino ethylsulphonylamino, dimethylsulphonylamino, diethylsulphonylamino, sulphonylamino (—NHSO$_2$NH$_2$), methylaminosulphonylamino, ethylaminosulphonylamino, dimethylaminosulphonylamino, diethylaminosulphonylamino, methylaminocarbonylamino, ethylaminocarbonylamino, dimethylaminocarbonylamino diethylaminocarbonylamino, acetylamino, aminomethylcarbonylamino, acetylaminomethyl, methoxycarbonylamino, ethoxycarbonylamino, t-butoxycarbonylamino, pyrrolidinyl, piperidinyl, piperazinyl, 4-methylpiperazinyl, homopipeprazinyl, morpholinyl, pyrrolidinylC$_{1-6}$alkyl, piperidinylC$_{1-6}$alkyl, piperazinylC$_{1-6}$alkyl, morpholinylC$_{1-6}$alkyl, 2-pyrrolidinylethylamino, 2-(1-methylpyrrolidinyl)ethylamino, 1-ethylpyrrolidinylmethylamino, piperidinylamino, 1-benzylpiperidinylamino, 4-(methoxy)phenylamino, 4-(3-hydroxypropyl)phenylamino, benzylamino, benzyloxy, pyridiylmethylamino group.

It will be appreciated that where two or more $R^{12}$ substituents are present, these need not necessarily be the same atoms and/or groups.

In general, when $R^8$ is a heteroaliphatic, heterocycloaliphatic or heteroaromatic group it is attached to the remainder of the molecule of formula (1) through any available heteroatom or group or, preferably, carbon atom.

The groups $R^2$, $R^3$, $R^7$ and additionally $R^{10}$ and/or $R^{10a}$ [where present] in compounds of formula (1) may each individually be an optionally substituted aliphatic, cycloaliphatic, heteroaliphatic, heterocycloaliphatic, aromatic or heteroaromatic group. In each case, the aliphatic, cycloalphatic, heteroaliphatic, heterocycloaliphatic, aromatic or heteroaromatic group may be as particularly described above for $R^8$ when it represents one of these groups.

Halogen atoms represented by the groups $R^2$, $R^3$ and/or $R^6$ in compounds of formula (1) include for example fluorine, chlorine, bromine or iodine atoms.

Substituted amino groups represented by the groups $R^1$, $R^2$, $R^3$ and/or $R^6$ in compounds of formula (1) include groups such as —NHR$^{15}$ [where $R^{15}$ is an optionally substituted straight or branched $C_{1-6}$alkyl, $C_{2-6}$alkenyl or $C_{2-6}$alkynyl group], —NR$^{15}$R$^{16}$ [where $R^{15}$ and $R^{16}$ are the same or different and $R^{16}$ is an optionally substituted alkyl, alkenyl or alkynyl group as just described for $R^{15}$], —N(R$^{17}$)COR$^{15}$, [where $R^{17}$ is a hydrogen atom or a group $R^{15}$ as just described], —N(R$^{17}$)SO$_2$R$^{18}$ [where $R^{18}$ is as described for $R^{17}$] —N[SO$_2$R$^{18}$]$_2$, —N(R$^{17}$)SO$_2$NR$^{17}$R$^{18}$, —N(R$^{17}$)CONR$^{17}$R$^{18}$, or —N(R$^{17}$)CSNR$^{17}$R$^{18}$. Particular examples of $R^{15}$, $R^{16}$, $R^{17}$ and $R^{18}$ alkyl, alkenyl or alkynyl groups include optionally substituted methyl, ethyl, n-propyl, i-propyl, allyl or ethynyl groups. Optional substituents include those described above in relation to the group $R^8$ when $R^8$ is an optionally substituted aliphatic group.

Particular examples of substituted amino groups represented by $R^2$, $R^3$ and/or $R^6$ include —NHCH$_3$, —N(CH$_3$)$_2$, —NHCH$_2$CH$_3$, —N(CH$_2$CH$_3$)$_2$, —NHCOCH$_3$, —NHSO$_2$H, —NHSO$_2$CH$_3$, —NHSO$_2$ NH$_2$, —NHSO$_2$ NHCH$_3$, —NHSO$_2$N(CH$_3$)$_2$, —NHCONH$_2$, —NHCONHCH$_3$ or —NHCONHCH$_2$CH$_3$ groups.

Optionally substituted straight or branched alkyl, alkenyl or alkynyl groups represented by $R^5$ and/or $R^{6a}$ [when present] include optionally substituted $C_{1-6}$alkyl, $C_{2-6}$alkenyl or $C_{2-6}$alkynyl as described above for $R^8$ aliphatic groups.

Straight or branched alkyl groups represented by the group $R^4$ in compounds of the invention include straight or branched $C_{1-6}$alkyl groups such as methyl or ethyl groups.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

It will be appreciated that depending on the nature of the substituents $R^1$–$R^3$ and $R^5$–$R^7$ the compounds of formula (1) may exist as geometrical isomers and/or may have one or more chiral centres so that enantiomers or diasteromers may exist. It is to be understood that the invention extends to all such isomers of the compounds of formula (1), and to mixtures thereof, including racemates.

In one class of compounds of formula (1) the groups $R^1$, $R^2$, $R^3$, $R^4$, $R^5$, $R^7$ and X are as defined for formula (1), and $R^6$ is a hydrogen or halogen atom or a group —$X^1$—$R^{6a}$.

In a further preferred class of compounds of formula (1) $R^4$ is especially a hydrogen atom.

The groups $R^5$ and $R^6$ in compounds of formula (1) are each preferably a hydrogen atom.

$R^7$ in compounds of formula (1) is preferably an optionally substituted aromatic or heteroaromatic group.

A further class of compounds according to the invention has the formula 1 (a):

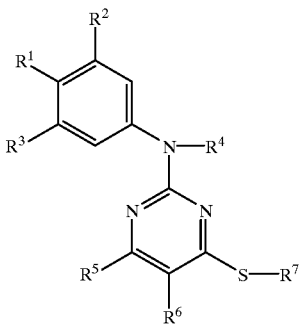

1(a)

wherein each of $R^1$, $R^2$, $R^3$, $R^4$, $R^5$, $R^6$ and $R^7$ is as defined for formula (1); and the salts, solvates, hydrates and N-oxides thereof.

In these compounds, $R^4$ and $R^5$ is each preferably a hydrogen atom. $R^6$ is preferably a group —$X^1R^{6a}$ where $X^1$ is as defined for formula (1) and $R^{6a}$ is an optionally substituted straight or branched chain alkyl group, or $R^6$ is especially a hydrogen atom. $R^7$ in compounds of formula (1a) is preferably an optionally substituted aromatic or heteroaromatic group.

The aromatic or heteroaromatic $R^7$ group in compounds of formulae (1) or 1 (a) in general may be as defined previously for compounds of formula (1). In one preference, however, $R^7$ is an optionally substituted phenyl, 1- or 2-naphthyl or heteroaromatic group containing one or two oxygen, sulphur and/or nitrogen atoms. Thus in particular $R^7$ may be an optionally substituted phenyl, 1- or 2-naphthyl, pyrrolyl, furyl, thienyl, indolyl, pyrazolyl, thiazolyl, [2,3-dihydro]benzofuryl, benzothiazolyl, 2-pyridyl, 3-pyridyl or 4-pyridyl group. Particularly useful groups include optionally substituted phenyl, particularly 3-substituted phenyl groups, 2-pyridyl, 3-pyridyl or 4-pyridyl groups. The aromatic or heteroaromatic group may in particular be attached to the remainder of the compound of formula (1) through any available ring carbon atom.

In general, the optional substituents which may be present on aromatic or heteroaromatic $R^7$ groups in compounds of formulae (1) or (1a) include one, two, or three $R^{12}$ substituents as generally and particularly described above and hereinafter in the Examples. Particularly useful $R^{12}$ substituents include —$NHR^{14}$, —$AlkNH_2$, —$AlkNHR^{14}$, —$OR^{14}$, —$AlkCO_2H$ or —$AlkCO_2Alk^1$ groups where $R^{14}$, Alk and $Alk^1$ are as generally and particularly defined above. Useful members of these substituents include those wherein $R^{14}$ is an —Alk, —$AlkNH_2$ or —Alk-heterocycloalkyl group. In these, and the other preferred substituents just mentioned, Alk and $Alk^1$ when present is each preferably a $C_{1-6}$alkyl group.

In the compounds of formula (1) and (1a) $R^1$ is preferably an —$R^8$ or in particular an —$OR^8$ group. The group $R^1$ is preferably attached at the 3- or 4- position of the phenyl ring. When $R^1$ is at the 3- position any $R^2$ and/or $R^3$ substituent is preferably at the 4- and/or 5- positions. When $R^1$ is at the 4- position any $R^2$ and/or $R^3$ substituent is preferably attached at the 3- and/or 5- positions.

Particularly useful —$R^8$ groups include heterocycloaliphatic groups of the type generally described above, especially optionally substituted $C_{3-7}$ cycloalkyl groups containing one or two heteroatoms such as pyrrolidinyl or morpholinyl groups. Particularly useful —$OR^8$ groups include optionally substituted alkoxy groups such as optionally substituted ethoxy groups. Particularly useful substituents include amino or substituted amino groups or, especially, —$NHet^1$ groups where —$NHet^1$ is as defined above.

In these last compounds, and in general, the groups $R^2$ and $R^3$ is each preferably a methyl or methoxy group or a hydrogen atom.

Particularly useful compounds according to the invention are:

4-(3-methoxyphenylsulphanyl)-N{[3,5-dimethyl4(2-(pyrrolidin-1-yl)-ethoxy]phenyl}-2-pyrimidineamine;

4-(3-Carboxyphenylsuphanyl)-N-{[3,5-dimethyl-4-(2-pyrrolidin-1-yl) -ethoxy]phenyl}-2-pyrimidineamine;

N-[4,5-Dimethoxy-3-(2-pyrrolidin-1-ylethoxy)]-4-(3-methoxyphenylsulphanyl)-2-pyrimidineamine;

4-(3-Methoxyphenylsulphanyl)-N-{4-methoxy-[3-(2-pyrrolidin-1-yl)-ethoxy]phenyl}2-pyrimidineamine;

N-{3,5-Dimethoxy-4-[2-(pyrrolidin-1-yl)ethoxy]phenyl}-4-(3-methoxyphenylsulphanyl)-2-pyrimidineamine;

N-{[4,5-Dimethoxy-3-(2-pyrrolin-1-yl)ethoxy]phenyl}4-(4-fluorophenylsulphanyl) pyrimidine-2-amine;

4-(3-Bromophenylsulphanyl)-N-[4,5-dimethoxy-3-(2-pyrrolidin-1-yl-ethoxy)phenyl]-2-pyrimidineamine;

N-{3,5-Dichloro-4-[(2-pyrrolidin-1-yl)ethoxy]phenyl}-4-(3,5-dimethylphenylsulphanyl)-2-pyrimidineamine;

and the salts, solvates and hydrates thereof.

Compounds according to the invention are potent and selective inhibitors of protein kinases, especially those of the src family, as demonstrated by their inhibition of enzymes such as $p56^{lck}$ and $p59^{fyn}$. The ability of the compounds to act in this way may be simply determined by employing tests such as those described in the Examples hereinafter.

The compounds according to the invention are thus of particular use in the prophylaxis and treatment of diseases in which inappropriate protein tyrosine kinase action plays a role, for example in autoimmune diseases such as rheumatoid arthritis, multiple sclerosis, and systemic lupus erythematosus, in transplant rejection, in graft v host disease, in hyperproliferative disorders such as tumours, psoriasis, in pannus formation in rheumatoid arthritis, restenosis following angioplasty and atherosclerosis, in osteoporosis and in diseases in which cells receive pro-inflammatory signals such as asthma, inflammatory bowel disease and pancreatitis.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $R^1$–$R^7$ when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups.

Thus according to one aspect of the invention, a compound of formula (1) wherein $R^4$ is a hydrogen atom may be prepared by displacement of a leaving atom or group in a pyrimidine of formula (2):

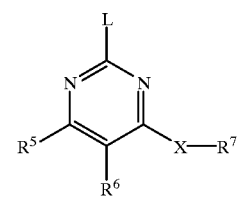

(2)

[where L is a leaving atom or group] with an aniline of formula (3):

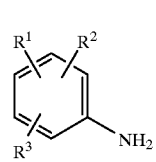

(3)

Particular leaving atoms or groups represented by L include for example halogen atoms, e.g. bromine, iodine or chlorine atoms, and sulphonyloxy groups, e.g. alkylsulphonyloxy groups, such as trifluoromethylsulphonyloxy, and arylsulphonyloxy groups, such as p-toluenesulphonyloxy.

The reaction may be performed at an elevated temperature, for example the reflux temperature, where necessary in the presence of a solvent, for example a ketone such as acetone, an alcohol such as ethanol or 2-ethoxyethanol or an aromatic hydrocarbon such as toluene, optionally in the presence of a base, for example an organic amine such as triethylamide or pyridine, or an acid, for example an inorganic acid such as hydrochloric acid.

Intermediate pyrimidines of formula (2) are either known readily available compounds or may be prepared by displacement of a leaving group from a pyrimidine of formula (4):

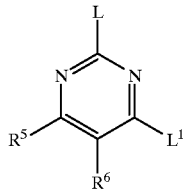

(4)

[where $L^1$ is a leaving atom or group as described above for the group L] using a thiol $R^7SH$. The reaction may be performed in the presence of a base such as sodium hydride in a solvent such as an amide, e.g. dimethylformamide at a low temperature of around 0° C.

The pyrimidines of formula (4) and the nucleophilic reagents $R^7SH$ are either known compounds or may be prepared using methods analogous to those used for the preparation of the known compounds.

The anilines of formula (3) are either known compounds or may be obtained by conventional procedures, for example by hydrogenation of the corresponding nitro derivatives using for example hydrogen in the presence of a metal catalyst in a suitable solvent, for example as more particularly described in the interconversion reactions discussed below, or by use of the corresponding nitro derivative and a reducing agent such as sodium hydrosulphite in a solvent such as ethanol at an elevated temperature such as the reflux temperature. The nitrobenzenes for this particular reaction are either known compounds or may be prepared using similar methods to those used for the preparation of the known compounds, for example by treatment of the corresponding benzene with nitric acid in the presence of an acid such as acetic acid at around ambient to the reflux temperature.

Compounds of formula (1) may also be prepared by interconversion of other compounds of formula (1) and it is to be understood that the invention extends to such interconversion processes. Thus, for example, standard substitution approaches employing for example alkylation, arylation, acylation, thioacylation, sulphonylation, formulation or coupling reactions may be used to add new substituents to and/or extend existing substituents in compounds of formula (1). Alternatively existing substituents in compounds of formula (1) may be modified by for example oxidation, reduction or cleavage reactions to yield other compounds of formula (1).

The following describes in general terms a number of approaches which can be employed to modify existing $R^1$, $R^2$, $R^3$, $R^4$, $R^5$, $R^6$ and/or $R^7$ groups in compounds of formula (1). It will be appreciated that each of these reactions may only be possible where an appropriate functional group exists in a compound of formula (1). Equally, any of the following reactions may be used to generate appropriately substituted intermediates of formulae (2), (3) and (4) for use in the preparation of compounds of formula (1).

Thus, for example alkylation or arylation of a compound of formula (1) may be achieved by reaction of the compound with a reagent $R^8L$ (where $R^8$ is as defined above except for a hydrogen atom) or $(R^{13})_m AlkL$ where L is as previously defined.

The alkylation or arylation reaction may be carried out in the presence of a base, e.g. an inorganic base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran, at around 0° C. to around 40° C.

In a variation of this process the leaving group L may be alternatively part of the compound of formula (1) and the reaction performed with an appropriate nucleophilic reagent such as an amine in a solvent such as an alcohol, e.g. ethanol, or an amide such as dimethylformamide at an elevated temperature, e.g. the reflux temperature.

In another general example of an interconversion process, a compound of formula (1) may be acylated or thioacylated. The reaction may be performed for example with an acyl halide or anhydride in the presence of a base, such as a tertiary amine e.g. triethylamine in a solvent such as a halogenated hydrocarbon, e.g. dichloromethane or carbon tetrachloride, or an alcohol, e.g. methanol at for example ambient temperature, or by reaction with a thioester in an inert solvent such as tetrahydrofuran at a low temperature such as around 0° C. The reaction is particularly suitable for use with compounds of formula (1) containing primary or secondary amino groups.

In a further general example of an interconversion process, a compound of formula (1) may be formulated, for example by reaction of the compound with a mixed anhydride $HCOOCOCH_3$ or with a mixture of formic acid and acetic anhydride.

Compounds of formula (1) may be prepared in another general interconversion reaction by sulphonylation, for example by reaction of the compound with a reagent $(R_{13})_m AlkS(O)_2L$, or $R^8S(O)_2L$ in the presence of a base, for example an inorganic base such as sodium hydride in a solvent such as an amide, e.g. a substituted amide such as dimethylformamide at for example ambient temperature. The reaction may in particular be performed with compounds of formula (1) possessing a primary or secondary amino group. In further examples of interconversion reactions according to the invention compounds of formula (1) may be prepared from other compounds of formula (1) by modification of existing functional groups in the latter.

Thus in one example, ester groups $—CO_2Alk^1$ in compounds of formula (1) may be converted to the corresponding acid $[—CO_2H]$ by acid- or base-catalysed hydrolysis or by catalytic hydrogenation depending on the nature of the group $Alk^1$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol. Catalytic hydrogenation may be carried out using for example hydrogen in the presence of a metal catalyst, for example palladium on a support such as carbon in a solvent such as an ether, e.g. tetrahydrofuran or an alcohol, e.g. methanol. Similarly, base-catalysed hydrolysis with for example an alkali metal hydroxide such as sodium hydroxide in a solvent such as an alcohol e.g. ethanol may be used to convert a $>NSO_2Alk(R^{13})_m$ or $>NSO_2R^8$ group to a $>N—H$ group.

In a second example, $—OAlk^2$ [where $Alk^2$ represents an alkyl group such as a methyl group] groups in compounds of formula (1) may be cleaved to the corresponding alcohol $[—OH]$ by reaction with boron tribromide in a solvent such as a halogenated hydrocarbon, e.g. dichloromethane at a low temperature, e.g. around −78° C.

Alcohol [—OH] groups may also be obtained by hydrogenation of the corresponding —OCH$_2$R$^8$ group in which R$^8$ is an aromatic group using for example hydrogen in the presence of a metal catalyst, for example palladium on a support such as carbon in a solvent such as ethanol in the presence of ammonium formate. In another example, —OH groups may be generated from the corresponding ester [—CO$_2$Alk] by reduction using for example a complex metal hydride such as lithium aluminium hydride.

In a further example, alcohol —OH groups in compounds of formula (1) may be converted to a corresponding —OAlk (R$^{13}$)$_m$ or —OR$^8$ group where R$^8$ is as described for formula (1) other than a hydrogen atom by coupling with a reagent (R$^{13}$)$_m$AlkOH or R$^8$OH in a solvent such as tetrahydrofuran in the presence of a phosphine, e.g. triphenylphosphine and an activator such as diethyl-, diisopropyl-, or dimethylazodicarboxylate.

In another example of an interconversion reaction, amines of formula (1) may be alkylated using a reductive alkylation process employing an aldehyde and a borohydride, for example sodium triacetoxyborohydride, in a solvent such as dichloromethane, in the presence of an acid such as acetic acid at around ambient temperature.

In a further example, amide groups in compounds of formula (1) may be obtained by coupling an acid [—CO$_2$H] or an active derivative thereof, e.g. an acid anhydride, ester, imide or halide, with an amine in which either the acid or amine forms part of the starting material of formula (1). The coupling reaction may be performed using standard conditions for reactions of this type. Thus for example the reaction may be carried out in a solvent, for example an inert organic solvent such as an amide, e.g. a substituted amide such as dimethylformamide, at a low temperature, e.g. −30° C. to ambient temperature, optionally in the presence of a base, e.g. an organic base such as a cyclic amine, e.g. N-methylmorpholine, and where necessary in the presence of a condensing agent, for example a diimide such as 1-(3-dimethylaminopropyl)-3-ethylcarbodiimide advantageously in the presence of a catalyst such as a N-hydroxy compound, e.g. a N-hydroxytriazole such as hydroxyazabenzotriazole.

Urea groups in compounds of formula (1) may be prepared by reaction of a corresponding amine [—NH$_2$] with an isocyanate, e.g. ethyl isocyanate, in a solvent, e.g. dichloromethane, at ambient temperature Aminosulphonylamino [—NHSO$_2$NH$_2$] groups in compounds of formula (1) may be obtained, in another example, by reaction of a corresponding amine [—NH$_2$] with sulphamide in the presence of an organic base such as pyridine at an elevated temperature, e.g. the reflux temperature.

In a further example, amine [—NH$_2$] groups in compounds of formula (1) may be obtained by hydrolysis from a corresponding imide by reaction with hydrazine in a solvent such as an alcohol, e.g. ethanol at ambient temperature.

In another example, a nitro [—NO$_2$] group may be reduced to an amine [—NH$_2$], for example by catalytic hydrogenation as just described, or by chemical reduction using for example a metal, e.g. tin or iron, optionally in the presence of an acid such as hydrochloric acid and a solvent such as an alcohol, e.g. methanol or ethanol.

In a further example of an interconversion process, a tetrazole substituent may be obtained from the corresponding nitrile by treatment of the latter with an azide, e.g. sodium azide, in a solvent such as a substituted amine, e.g. dimethylformamide at an elevated temperature.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid or 3-chloroperoxybenzoic acid in a solvent, e.g. dichloromethane, at ambient temperature.

Where salts of compounds of formula (1) are desired, these may be prepared by conventional means, for example by reaction of a compound of formula (1) with an appropriate acid or base in a suitable solvent or mixture of solvents, e.g. an organic solvent such as an ether, e.g. diethylether, or an alcohol, e.g. ethanol.

The following Examples illustrate the invention. In the Examples all [1] Hnmr were run at 300 MHz unless specified otherwise. All temperatures are in ° C. The following abbreviations are used: DMSO—dimethylsulphoxide; DMF—dimethylformamide. In many of the following Examples 2-chloro-4-(3-methoxyphenylsulphanyl) pyrimidine is used as a starting material.

The preparation of this compound is described in Example 1. Where it is used in other Examples it is referred to as Intermediate A.

EXAMPLE 1

4-{3-Methoxyphenylsulphanyl)N- [3,5-dimethyl-4 (2-pyrrolidin-1-yl)-ethoxy]phenyl}-2-pyrimidineamine dihydrochloride A mixture of 2-chloro-4-(3-methoxyphenylsulphanyl) pyrimidine (140 mg, 0.55 mmol) and 3,5-dimethyl-4-(2-(1-pyrrolidino)ethoxy)aniline (130 mg, 0.55 mmol) was heated at reflux under a nitrogen atmosphere in ethoxyethanol (4 ml) containing 1M hydrochloric acid in diethyl ether (0.55 ml), for 2 h. After this time the solvent was removed under reduced pressure, the residue partitioned between CH$_2$Cl$_2$ and saturated aqueous NaHCO$_3$ solution, and the organic phase was dried (MgSO$_4$) and concentrated. The residue was subjected to column chromatography (silica, 5% methanol—CH$_2$Cl$_2$) and the product dissolved in ethyl acetate (5 ml) and treated with 1M hydrochloric acid in diethyl ether. The resulting precipitate was collected and dried to give the title compound (100 mg) as a yellow solid m.p. 94–96°. δ$_H$ (d$^6$ DMSO) 11.21 (1H, br s), 9.73 (1H, br s), 8.17 (1H, d, J 5.6 Hz), 7.46–7.41 (1H, m), 7.23 (2H, s), 7.21–7.18 (2H, m), 7.13–7.10 (1H, m), 6.34 (1H, d, J 5.2 Hz), 4.34 (1H, br s), 4.10–4.04 (2H, m), 3.75 (3H, s), 3.65–3.53 (4H, m), 3.20–3.11 (2H, m), 2.16 (6H, s) and 2.02–1.94 (4H, m).

The 2-chloro-4-(3-methoxyphenylsulphanyl)pyrimidine used as starting material was prepared by adding a solution of 3-methoxybenzenethiol (0.84 ml, 6.71 mmol) in dry DMF (30 ml) to a suspension of sodium hydride [60% dispersion in oil] (295 mg, 7.40 mmol) in DMF (30 ml) at 0°, and stirring for 10 min before addition of 2,4-dichloropyrimidine (1.0 g, 6.71 mmol). After continued stirring at 0° for 2 h, the solvent was removed under reduced pressure and the residue partitioned between ethyl acetate (100 ml) and 1M aqueous NaOH (75 ml). The organic layer was dried, concentrated under reduced pressure and the residue subjected to column chromatography. The resulting oil was taken up in diethyl ether-hexane to give the desired product (1.08 g) as a white solid, m.p. 65–66°. δ$_H$ (CDCl$_3$) 8.18 (1H, d, J 5.4 Hz), 7.41 (1H, t, J 8.09 Hz), 7.20–7.05 (3H, m), 6.65 (1H, d, j 5.4 Hz) and 3.85 (3H, s).

The compounds of Examples 2 and 3 were prepared in a similar manner:

EXAMPLE 2

N-(4-(2-Dimethylaminoethoxy)phenyl)-4-(4-methoxyphenylsulphanyl)-2-pyrimidineamine from 4-(2-dimethylaminoethoxy)aniline (180 mg, 1.0 mmol), 2-chloro-4-(4-methoxyphenylsulphanyl)pyrimidine (253 mg, 1.0 mmol) and 1M hydrochloric acid in diethyl ether (1.0 ml, 1.0 mmol) to give the title compound (160 mg) as a white solid m.p. 112–113°. δH (CDCl$_3$) 7.99 (1H, d, J 5.4 Hz), 7.51 (2H, d, J 8.7 Hz), 7.27 (2H, d, J 9.0 Hz), 6.99–6.96 (3H, m), 6.78 (2H, d, J 9.0 Hz), 6.23 (1H, d, J 5.4 Hz), 4.04 (2H, t, J 5.7 Hz), 3.87 (3H, s), 2.73 (2H, t, J 5.7 Hz) and 2,34 (6H, s).

The 2-chloro4-(4-methoxyphenylsulphanyl)pyrimidine was prepared in a similar manner to the analogous starting material of Example 1, from 4-methoxybenzenethiol (1.90 g, 13.4 mmol), 2,4-dichloropyrimidine (2.0 g, 13.4 mmol) and sodium hydride [60% dispersion in oil] (590 mg, 14.8 mmol) as an off-white solid m.p. 69–70°.

EXAMPLE 3

4-(3-Methoxyphenylsulphanyl)-N-[3-(4-methylpiperazinyl)phenyl]-2-pyrimidneamine

From Intermediate A (436 mg, 1.72 mmol), 3-(4-methylpiperazin-1-yl)aniline (330 mg, 1.72 mmol) and 1M hydrogen chloride in diethyl ether (1.72 ml) to give the title compound (70 mg) as a yellow solid m.p. 105–106°. δH (CDCl$_3$) 8.04 (1H, d, J 5.4 Hz), 7.04–6.95 (2H, m), 6.59 (1H, dd, J 8.0, 1.8 Hz), 6.26 (1H, d, J 5.4 Hz), 3.81 (3H, s), 3.23–3.19 (4H, m), 2.58–2.54 (4H, m) and 2.34 (3H, s).

EXAMPLE 4

N-4-Hydroxyphenyl):4-(4-methylphenylsulphanyl)-2-pyrimidineamine

A mixture of 2-chloro4-(4-methylphenylsulphanyl) pyrimidine (1 00 mg, 0.42 mmol) and 4-aminophenol (55 mg, 0.5 mmol) was heated at reflux in ethoxyethanol (2 ml) for 1.5 h. The reaction was concentrated under reduced pressure and subjected to column chromatography [silica, 20% ethyl acetate—CH$_2$Cl$_2$] to give the title compound (60 mg) as a buff solid m.p. 179–180°. δH (CDCl$_3$) 8.01 (1H, d, J 5.4 Hz), 7.50–7.45 (2H, m), 7.31–7.27 (4H, m), 6.93 (1H, br s), 6.71–6.66 (2H, m), 6.25 (1H, d, J 5.4 Hz), 4.70 (1H, br s) and 2.44 (3H, s).

The 2-chloro-4-(4-methylphenylsulphanyl)pyrimidine was prepared in a similar manner to the analogous starting material of Example 1, from p-thiocresol (838 mg, 6.72 mmol), 2,4-dichloropyrimidine (1.0 g, 6.71 mmol) and sodium hydride [60% dispersion in oil] (295 mg, 7.4 mmol), m.p. 80–81°. δH (CDCl$_3$) 8.15 (2H, d, J 5.4 Hz), 7.46 (2H, d, J 8.0 Hz), 7.30 (2H, d, J 8.0 Hz), 6.59 (1H, d, J 5.4 Hz) and 2.43 (3H, s).

The compounds of Examples 5–17 were prepared in a similar manner to the compound of Example 4:

EXAMPLE 5

N-(4-Benzyloxyphenyl)-4-(4-methoxyphenylsulphanyl)-2-pyrimidine from 2-chloro-4-(4-methoxyphenylsulphanyl)pyrmidine (7.51 g, 6.0 mmol—see Example 2) and 4-benzyloxyaniline (2.83 g, 112.9 mmol) to give the title compound (1.60 g) as a white solid m.p. 146–147°. δH (CDCl$_3$) 8.00 (1H, d, j 5.4 Hz), 7.53 (2H, d, J 8.8 Hz), 7.45–7.27 (7H, m), 7.02–6.96 (3H, m), 6.85 (2H, d, J 9.0 Hz), 6.24 (1H, d, J 5.4 Hz), 5.04 (2H, s) and 3.88 (3H, s).

EXAMPLE 6

4-(3-Methoxyphenylsulphanyl)-N-(4-morpholinophenyl)-2-pyrimidineamine from Intermediate A (300 mg, 1.19 mmol) and 4-morpholinoaniline (211 mg, 1.19 mmol) to give the title compound as an off-white solid m.p. 159–161°. δH (CDCl$_3$) 8.01 (1H, dd, J 5.3, 2.7 Hz), 7.40–7.37 (3H, m), 7.33 (1H, dd, J 6.5, 2.1 Hz), 7.30 (1H, br s), 7.05–7.01 (1H, m), 6.96 (1H, s), 6.80 (2H, d, J 8.9 Hz), 6.27 (1H, dd, J 5.3, 2.7 Hz), 3.88–3.83 (4H, m), 3.80 (3H, s), 3.11–3.08 (4H, m).

EXAMPLE 7

N-3-Hydroxyphenyl)-4-(3-methoxyphenylsulphanyl)-2-pyrimidineamine hydrochloride

From Intermediate A (1.0 g, 3.96 mmol) and 3-aminophenol (437 mg, 4.0 mmol) to give the title compound (930 mg) as a white solid m.p. 144–145°. δH (CDCl$_3$) 8.06 (1H, d, J 5.4 Hz), 7.39 (1H, t, J 7.9 Hz), 7.26–7.03 (5H, m), 6.71(1H, dd, J 7.9, 1.6 Hz), 6.46 (1H, dd, J 7.9, 2.4 Hz), 6.42 (1H, d, J 5.4 Hz), 5.57 (1H, br s) and 3.82 (3H, s).

EXAMPLE 8

N-(4-Carboxyphenyl)-4-(3-methoxyphenylsulphanyl)pyrimidine-2-amine hydrochloride From Intermediate A (500 mg, 1.98 mmol) and 4-aminobenzoic acid (274 mg, 2.0 mmol) to give the title compound (350 mg) as a yellow solid m.p. 242–243°. δH (d$^6$ DMSO) 10.21 (1H, br s), 8.25 (1H, d, J 5.5 Hz), 7.69 (2H, d, J 8.8 Hz), 7.56 (2H, d, J 8.8 Hz), 7.48 (1H, t, J 8.1 Hz), 7.23–7.16 (3H, m), 6.62 (1H, d, J 5.5 Hz) and 3.78 (3H, s).

EXAMPLE 9

N-(3-Hydroxy-4-methoxy)phenyl-4-(3-methoxyphenylsulphanyl)-2-pyrimidineamine

From Intermediate A (4.55 g, 18 mmol) and 5-amino-2-methoxyphenol (2.51 g, 18 mmol) to give the title compound as a yellow solid m.p. 182–183°. δH (CDCl$_3$) 10.40 (1H, br s), 7.77 (1H, d, J 6.6 Hz), 7.45–7.39 (1H, m), 7.15 (1H, d, J 7.8 Hz), 7.10–7.07 (2H, m), 6.99 (1H, d, J 2.5 Hz), 6.78 (1H, dd, J 8.7, 2.5 Hz), 6.65 (1H, d, J 8.7 Hz), 6.47 (1H, d, J 6.6 Hz), 5.63 (1H, br s), 3.87 (3H, s) and 3.78 (3H, s).

EXAMPLE 10

N-[3-(2-Hydroxyethyl)phenyl]-4-3-methoxyphenylsulphanyl)-2-pyrimidineamine

From Intermediate A (1.07 g, 4.2 mmol) and 3-aminophenethyl alcohol (576 mg, 4.2 mmol) to give the title compound (1.1 g) as a yellow solid m.p. 122–124°. δH (CDCl$_3$) 8.05 (1H, d, J 5.4 Hz), 7.40–7.30 (3H, m), 7.22–7.13 (4H, m), 7.03 (1H, ddd, J 8.3, 2.6, 1.0 Hz), 6.86 (1H, d, J 7.6 Hz), 6.32 (1H, d, J 5.4 Hz), 3.86–3.81 (5H, m) and 2.81 (2H, t, J 6.5 Hz).

EXAMPLE 11

N-[3-Hydroxy-5-(1,1,1-trifluoromethyl)phenyl]-4-(3-methoxyphenylsulphanyl)-2-pyrimidineamine hydrochloride From Intermediate A (2.0 g, 7.9 mmol) and 3-amino-5-(1,1,1-trifluoromethyl)phenyl (1.4 g, 7.9 mmol) to give the title compound (2.0 g) as a white solid m.p. 163–164°. δH (d$^6$ DMSO) 9.98 (1H, br s), 8.22 (1H, d, J 5.4 Hz), 7.56 (1H, s), 7.48–7.43 (2H, m), 7.24–7.21 (2H, m), 7.15–7.12 (1H, m), 6.66 (1H, s), 6.24 (1H, d, J 5.4 Hz) and 3.79 (3H, s).

EXAMPLE 12

N-(3-Hydroxymethyl)phenyl-4-(3-methoxyphenylsulphanyl)-2-pyrimidineamine hdyrochloride From Intermediate A (3.79 g, 15 mmol) and 3-aminobenzyl alcohol (1.85 g, 15 mmol) to give the title compound (3.14 g) as a yellow solid m.p. 124–125°. δH (d$^6$ DMSO) 10.18 (1H, br s), 8.22 (1H, d, J 5.7 Hz), 7.88 (1H, br s), 7.49–7.36 (4H, m), 7.22–7.14 (3H, m), 7.07 (1H, t, J 7.7 Hz), 6.93 (1H, d, J 7.6 Hz), 6.52 (1H, d, J 5.7 Hz), 4.41 (2H, s) and 3.77 (3H, s).

EXAMPLE 13

N-(3-Aminomethylphenyl)4-(3-methoxyphenylsulphanyl)-2-pyrimidineamine

From Intermediate A (2.53 g, 10 mmol) and 3-aminobenzylamine hydrochloride (1.59 g, 10 mmol) to give the title compound (1.5 g) as a yellow solid m.p. 120–121°. δH (d$^6$ DMSO) 10.11 (1H, br s), 8.54 (3H, br s), 8.23 (1H, d, J 5.6 Hz), 7.52–7.44 (3H, m), 7.22–7.15 (5H, m), 6.50 (1H, d, J 5.6 Hz), 3.88–3.86 (2H, br m) and 3.77 (3H, s).

EXAMPLE 14

N-(3-Chloro-4-hydroxy-5-methyl)-4-(3-methoxyphenylsulphanyl)pyrimidine

From Intermediate A (0.5 g, 1.98 mmol) and 4-amino-2-chloro-6-methylphenol (312 mg, 1.98 mmol) to give the title compound (247m) as a yellow solid m.p. 161°. δH (d$^6$ DMSO) 9.87 (1H, br s), 8.13 (1H, d, J 5.3 Hz), 7.48 (1H, s), 7.38 (2H, m), 7.21–7.16 (3H, m), 7.11 (1H, m), 6.31 (1H, d, J 5.3 Hz), 3.72 (3H, s) and 2.13 (3H, s).

EXAMPLE 15

4-(3-Bromophenylsulphanyl)-N-(3-nitrophenyl)-2-pyrimidineamine

From 4-(3-bromophenylsulphanyl)-2-chloropyrimidine (3.0 g, 9.95 mmol) and 3-nitroaniline (1.38 g, 9.95 mmol) to give the title compound (3.2 g) as a yellow solid m.p. 208–209°. δH (d$^6$ DMSO) 10.23 (1H, s), 8.51 (1H, s), 8.28 (1H, d, J 5.4 Hz), 7.89–7.69 (5H,m), 7.47 (1H, t, J 7.5 Hz), 7.39 (1H, t, J 7.4 Hz) and 6.58 (1H, d, J 5.4 Hz).

The chloropyrimidine starting material was prepared in a similar manner to Intermediate A as a colorless solid m.p. 60–61°. δH (CDCl$_3$) 8.23 (1H, d, J 5.4 Hz), 7.76 (1H, t, J 1.8 Hz), 7.65 (1H, ddd, J 7.9, 1.8, 1.1 Hz), 7.56–7.52 (1H, m), 7.37 (1H, t, J 7.8 Hz) and 6.70 (1H, d, J 5.4 Hz).

EXAMPLE 16

N-[3-(2-Hydroxyethoxy)phenyl]-4-(3-nitrophenylsulphanyl)-2-pyrimidineamine

From 2-chloro(3-nitrophenylsulphanyl)pyrimidine (1.0 g, 3.75 mmol prepared from 2,4-dichloropyrimidine and 3-nitrobenzenethiol according to the method of Example 1) and 3-aminophenethyl alcohol (514 mg 3.75 mmol) to give the title compound (350 mg) as a yellow powder m.p. 160–161. δH (CDCl$_3$) 8.46 (1H, t, J 1.9 Hz), 8.34–8.30 (1H, m), 8.11 (1H, d, J 5.3 Hz), 7.93–7.89 (1H, m), 7.62 (1H, t, J 8.0 Hz), 7.20–7.12 (3H, m), 7.03 (1H, t, J 7.8 Hz), 6.84 (1H, d, J 7.5 Hz), 6.48 (1H, d, J 5.3 Hz), 3.81 (2H, t, J 6.4 Hz) and 2.76 (1H, t, J 5.6 Hz).

EXAMPLE 17

4-(3-Carboxyphenylsuphanyl)-N-{[3,5-dimethyl-4-(2-pyrrolidin-1-yl)ethoxy]phenyl}-2-pyrimidineamine sodium salt From 4-(3-tert-butyoxycarbonylphenylsulphanyl)-2-chloropyrimidine (300 mg, 0.93 mmol) and 3,5-dimethyl-4-(2-pyrrolidinyl-1-yl)ethoxyaniline (234 mg, 1.0 mmol) to give the title compound (175 mg) as an off white solid m.p. 155–156°. δH (d$^6$ DMSO) 8.96 (1H, s), 8.14 (1H, d, J 5.2 Hz), 8.10–8.04.(2H, m), 7.79 (1H, d, J 7.9 Hz), 7.58 (1H, t, J 7.8 Hz), 7.17 (2H, s), 6.37 (1H, d, J 5.2 Hz), 4.74 (4H, br s), 3.82 (2H, t, J 6.1 Hz), 2.86 (3H, t, J 6.2 Hz), 2.64–2.62 (4H, br m), 2.13 (6H, s) and 1.74–1.72 (4H, br m).

The sodium salt was formed as a result of partitioning the crude reaction residue between saturated aqueous NaHCO$_3$ and chloroform. The salt was extracted into the organic phase.

The chloropyrimidine starting material was prepared by treating a solution of 4-(3-carboxyphenylsulphanyl)-2-chloropyrimidine (500 mg, 1.87 mmol) in CH$_2$Cl$_2$ (25 ml) with concentrated H$_2$SO$_4$ (5 drops), cooling to −78° and condensing isobutylene gas (approximately 10 g) into the reaction vessel.

After condensation was complete, the cold bath was removed and the solution left at room temperature for 4 h. The reaction was washed with 2M NaOH, dried (MgSO$_4$) and evaporated to give the desired material (300 mg) as a colorless gum which was used for the above process without purification.

4-(3-Carboxyphenylsulphanyl)-2-chloropyrimidine was prepared by heating a solution of 2,4-dichloropyrimidine (2.97 g, 19.9 mmol) and 3-mercaptobenzoic acid (3.07 g, 1 9.9 mmol) in ethanol (50 ml) at reflux for 1 h. On cooling to 0°, the resulting precipitate was collected and dried to give the desired material (3.38 g) as a white solid.

EXAMPLE 18

N-[3-(2-Diethylaminoethoxy)phenyl]-4-(3-methoxyphenylsulphanyl)-2-pyrimidineamine To a solution of the compound of Example 7 (325 mg, 1.0 mmol) in DMF (15 ml) was added 2-diethylaminoethyl chloride hydrochloride (189 mg, 1.1 mmol) and caesium carbonate (717 mg, 2.2 mmol) and the resulting mixture heated at 100° for 4 h. After this time the solvent was removed under reduced pressure to give a residue which was partitioned between CH$_2$Cl$_2$ (10 ml) and brine (2×100 ml). The organic phase was dried (MgSO$_4$) and evaporated under reduced pressure to give a residue which was subjected to column chromatography (silica; 5% methanol in CH$_2$Cl$_2$) to give a colourless gum. This was taken up in ethyl acetate (25 ml) into which dry HCl gas was bubbled, and the resulting precipitate was collected and dried to give the title compound (113 mg) as a yellow powder, m.p. 192–193°. δH (d$^6$ DMSO) 10.72 (1H, br s), 9.84 (1H, br s), 8.19 (1H, d, J 5.4 Hz), 7.47 (1H, t, J 8.2 Hz), 7.31–7.06 (7H, m), 6.59 (1H, d, J 8.0 Hz), 6.37 (1H, d, J 5.4 Hz), 4.35–4.32 (2H, m), 3.78 (3H, s), 3.48–3.46 (2H, m), 3.19–3.16 (4H, m) and 1.25 (6H, t, J 7.2 Hz).

The compounds of Examples 19 and 20 were prepared in a similar manner using potassium carbonate in place of caesium carbonate.

EXAMPLE 19

N-[4,5-Dimethoxy-3(2-pyrrolidin-1-ylethoxy)phenyl]-4-(3-methoxyphenylsulphanyl)2-pyrimidineamine From N-(3,4-dimethoxy-5-hydroxyphenyl)-4-(3-methoxyphenylsulphanyl)-2-pyrimidineamine (500 mg, 1.3 mmol), 1-(2-chloroethyl)pyrrolidine hydrochloride (276 mg, 1.6 mmol) and potassium carbonate (591 mg, 4.2 mmol) to give the title compound (430 mg) as a yellow solid m.p. 120–121°. δH (d⁶ DMSO) 11.27 (1H, br s), 9.68 (1H, s), 8.18 (1H, d, J 5.4 Hz), 7.46 (1H, t, J 8.2 Hz), 7.23–7.18 (3H, m), 7.13 (1H, d, J 2.4 Hz), 7.11 (1H, d, J 2.4 Hz), 6.21 (1H, d, J 5.4 Hz), 4.31–4.27 (2H, m), 3.78 (3H, s), 3.72 (3H, s), 3.67 (3H, s), 3.63–3.56 (4H, m), 3.18–3.10 (2H, m), 2.08–2.01 (2H, m) and 1.98–1.90 (2H, m).

The pyrimidineamine starting material was prepared from Intermediate A (3.03 g, 12 mmol) and 5-amino-2,3-dimethoxyphenol (2.0 g, 11.8 mmol) in a similar procedure to Example 1 to give the desired product (1.0 g) as an off-white solid m.p. 153–154°.

5-Amino-2,3-dimethoxyphenol was prepared by hydrogenation of a solution of 1-benzyloxy-2,3-dimethoxy-5-nitrobenzene (2.5 g, 8.2 mmol) in ethanol (45 ml) over 10% palladium on charcoal (20 mg) at 20 psi and room temperature for 6 h. The catalyst was removed by filtration through a pad of Celite® washing thoroughly with methanol. The combined filtrate and washings were evaporated to give the desired product (1.3 g) as a dark grey solid.

1-Benzyloxy-2,3-dimethoxy-5-nitrobenzene was prepared by the method described in International Patent Specification No. WO97/19065.

EXAMPLE 20

4-(3-Methoxyphenylsulphanyl)-N-{4-methoxy-[3-(2-pyrrolidin-1-yl)ethoxyphenyl}2-pyrimidineamine From the compound of Example 9 (502 mg, 1.28 mmol), 1-(2-chloroethyl)pyrrolidine hydrochloride (262 mg, 1.54 mmol) and potassium carbonate (575 mg, 4.1 mmol) to give the title compound (135 mg) as a buff solid m.p. 147–149°. δH (d⁶ DMSO) 10.98 (1H, br s), 9.58 (1H, br s), 8.15 (1H, d, J 5.5 Hz), 7.45 (1H, m), 7.30 (1H, m), 7.18–7.16 (5H, m), 6.82 (1H, br s), 6.30 (1H, d, J 5.5 Hz), 4.25 (2H, br s), 3.77 (3H, s), 3.74 (3H, s), 3.56 (4H, br m) 3.12 (2H, m) and 2.00–1.82 (4H, m).

EXAMPLE 21

N-{3,5-Dimethoxy-4-[2-(pyrrolidin-1-yl)ethoxy]phenyl}-4-(3-methoxyphenylsulphanyl)-2-pyrimidineamine dihydrochloride To a solution of N-{3,5-dimethoxy-4-[2-(p-toluenesulphonyloxy)ethoxy]-phenyl}-4-(3-methoxyphenylsulphanyl)-2-pyrimidineamine (1.0 g, 1.76 mmol) in DMF (6 ml) was added pyrrolidine (2.9 ml) and the reaction heated at 70° for 2 h. After this time the solvent was removed under reduced presure and the residue partioned between ethyl acetate (100 ml) and saturated aqueous Na₂CO₃ (10 ml). The organic phase was dried (MgSO₄), concentrated under reduced pressure and the residue subjected to column chromatography (silica gel; 12% methanol—CH₂Cl₂). The resulting material was taken up in ethyl acetate and treated with hydrogen chloride gas to give a precipitate which was collected by filtration and dried to give the title compound (440 mg) as a yellow solid. δH (d⁶ DMSO) 10.67 (1H, br s), 9.72 (1H, s), 8.19 (1H, d, J 5.5 Hz), 7.45 (1H, t, J 8.1 Hz), 7.22 (2H, m), 7.16–7.11 (3H, m), 6.23 (1H, d, J 5.5 Hz), 4.12–4.08 (2H, m), 3.77 (3H, s), 3.73 (6H,s ), 3.69–3.62 (2H, m), 3.47–3.42 (2H, m), 3.20–3.10 (2H, m) and 2.05–1.93 (4H, m).

The tosylate used as starting material was prepared by treating a solution of N-[3,5-dimethoxy-4-(2-hydroxyethoxy)phenyl]-4-(3-methoxyphenylsulphanyl)-2-pyrimidineamine (2.0 g, 4.3 mmol) in pyridine (6 ml) with p-toluenesulphonyl chloride (3.28 g, 17.2 mmol) at room temperature for 2 h. Water (25 ml) was added to the reaction followed by acidification with 2M hydrochloric acid, and this was extracted with ethyl acetate (100 ml). The organic phase was washed with 2M hydrochloric acid (100 ml) and saturated aqueous Na₂CO₃ (100 ml), dried (MgSO₄) and concentrated under reduced pressure to give the desired product as a light brown oil (2.31 g). δH (CDCl₃) 8.04 (1H, d, J 5.4 Hz), 7.80 (2H, d, J 8.3 Hz), 7.39–7.30 (3H, s), 7.20–7.13 (2H, m), 7.03–6.99 (2H, m), 6.86 (2H, s), 6.22 (1H, d, J 5.4 Hz), 4.31 (2H, t, J 5.6 Hz), 4.13 (2H, t, J 5.6 Hz), 3.81 (3H, s), 3.77 (6H, s) and 2.43 (3H, s).

The hydroxyethoxy starting material was prepared from Intermediate A (2.27 g, 9.0 mmol) and 4-(2-hydroxyethoxy)-3,5-dimethoxyaniline (1.92 g, 9.0 mmol) using a similar method to the compound of Example 4 to give the title compound as a yellow solid (2.4 g) m.p. 173–179°.

EXAMPLE 22

4-(3-Methoxyphenylsulphanyl)-N-{4-N'-(2-pyrrolidin-1-yl)ethylcarboxamido]phenyl}-2-pyrimidineamine To a solution of the compound of Example 8 (1.0 g, 2.56 mmol) in dry DMF (10 ml) was added 1-(3-dimethylaminopropyl)-3-ethylcarbodiimide (541 mg, 2.82 mmol), hydroxyazabenzotriazole (383 mg, 2.82 mmol) and N-methylmorpholine (1.24 ml, 11.29 mmol) followed by 1-(2-aminoethyl)pyrrolidine (0.36 ml, 2.8.2 mmol) and the reaction stirred at room temperature for 4 h. After this time the reaction was concentrated under reduced pressure to give a yellow oil which was partitioned between brine (250 ml) and CH₂Cl₂ (250 ml). The organic phase was dried (MgSO₄) and evaporated to a sticky white solid which was taken up in hot ethyl acetate. The resulting solution was cooled, diluted carefully with hexane and the resulting precipitate collected and dried to give the title compound (620 mg) as a white solid m.p. 146–147°. δH (d⁶ DMSO) 9.92 (1H, br s), 8.39 (1H, br s), 8.23 (1H, d, J 5.3 Hz), 7.70–7.67 (2H, m), 7.60–7.57 (2H, m), 7.49 (1H, t, J 7.2 Hz), 7.24 (3H, m), 6.48 (1H, d, J 5.3 Hz), 3.79 (3H, s), 3.48 (2H, m), 2.90–2.81 (6H, m) and 1.83–1.76 (4H, m).

EXAMPLE 23

4-(3-Methoxyphenylsulphanyl)-N-[3-(2-pyrrolidin-1-yl)ethyl]-2-pyrimidineamine dihydrochloride From 4-(3-methoxyphenylsulphanyl)-N-[3-(2-p-toluenesulphonyloxyethyl)-phenyl]-2-pyrimidineamine (110 g) and pyrrolidine (5.1 ml, 62 mmol) in a manner analogous to the preparation of the compound of Example 21, to give the title compound (450 mg) as a yellow solid m.p. 136–1370. The tosylate starting material was prepared in a similar manner to the analogous intermediate of Example 21, from the compound of Example 10 (1.10 g, 3.1 mmol) and p-toluenesulphonyl chloride (2.36 g, 12.4 mmol) to give the desired compound (1.10 g) as a yellow oil which was used without purification.

EXAMPLE 24

N-{3-[2-(Pyrrolidin-1-yl)ethoxy]phenyl}-4-(3-methoxyphenylsulphanyl)-2-pyrimidineamine dihydrochloride From the compound of Example 11 (1.0 g, 2.3 mmol), 1-(2-chloroethyl) pyrrolidine hydrochloride (476 mg, 2.8 mmol) and potassium carbonate (780 mg, 5.6 mmol) using the method of Example 18 to give the title compound (320 mg) as an off-white solid m.p. 199–200°. δH (d⁶ DMSO) 11.04 (1H, br s),10.08 (1H, s), 8.25 (1H, d, J 5.4 Hz), 7.78 (1H, s), 7.71 (1H, s), 7.47 (1H, t, J 8.2 Hz), 7.24–7.21 (2H,m ), 7.16–7.13 (1H, m), 6.90 (1H, s), 6.28 (1H, d, J 5.5 Hz), 4.82 (1H, br s), 4.40 (2H, m), 3.78 (3H, s), 3.60–3.55 (4H, m), 3.14–3.08 (2H, br m) and 2.08–1.90 (4H, br m).

EXAMPLE 25

4-(3-Methoxyphenylsulphanyl)-N-(3-pyrrolidin-1-ylmethyl)phenyl pyrimidine-2-amine dihydrochloride To a suspension of the compound of Example 12 (465 mg, 1.24 mmol) in CHCl₃ (40 ml) was added thionyl chloride (0.3 ml, 1.36 mmol) and the resulting mixture heated at 55° for 6 h. The reaction was then diluted with CH₂Cl₂ (60 ml), washed with saturated aqueous NaHCO₃, dried (MgSO₄) and concentrated in vacuo to a yellow oil. This residue was dissolved in acetonitrile (25 ml), pyrrolidine (0.52 ml, 6.2 mmol) added and the solution heated at reflux for 0.5 h. The reaction was concentrated in vacuo and the residue was subjected to column chromatography (silica gel; 10% methanol in CH₂Cl₂). The resulting material was dissolved in an ethyl acetate/ethanol (1:10 v/v) mixture (10ml) and treated with 1M hydrogen chloride in diethyl ether (2 ml). The precipitate which formed was collected and dried to give the title compound (300 mg) as a yellow solid m.p. 115–116°. δH (d⁶ DMSO) 11.17 (1H, br s), 9.96 (1H, s), 8.21 (1H, d, J 5.4 Hz), 7.63–7.44 (3H, m), 7.29–7.15 (7H, m), 6.43 (1H, d, J 5.4 Hz), 4.21 (2H, d, J 5.6 Hz), 3.78 (3H, s0<3.90–3.80 (2H, br m), 3.05–2.94 (2H, br m) and 2.00–1.88 (4H, br m).

EXAMPLE 26

N-(3-Aminophenyl)-4-(3-bromophenylsulphanyl)-2-pyrimidineamine

The compound of Example 15 (3.0 g, 6.82 mmol) was dissolved in ethanol (50 ml) and tin (II) chloride dihydrate (4.62 g, 20.47 mmol) added. The reaction was heated at reflux for 3 h, after which time 2M aqueous NaOH (100 ml) was added and the resulting suspension extracted with ethyl acetate (200 ml). The organic phase was dried (MgSO₄) and evaporated to give the title compound (2.1 g) as a pale orange solid m.p. 109–110°. δH (CDCl₃) 8.07 (1H, d, J 5.3 Hz), 7.79 (1H, s), 7.61 (1H, d, J 8.0 Hz), 7.55 (1H, d, J 7.7 Hz), 7.33 (1H, t, J 7.9 Hz), 7.08 (1H, br s), 6.98 (1H, t, J 8.0 Hz), 6.87 (1H, s), 6.68 (1H, d, J 7.0 Hz), 6.37–6.31 (2H, m) and 3.59 (2H, br s).

EXAMPLE 27

N-{[4,5-Dimethoxy-3-(2-pyrrolin-1-yl)ethoxy]phenyl}4-(4-fluorophenylsulphanyl) pyrimidine-2-amine dihydrochloride In a manner analogous to the preparation of the compound of Example 21 from N-{4,5-dimethoxy-3-(2-p-toluenesulphonyloxy)ethoxy]phenyl}-4-(4-fluorophenyl-sulphanyl)pyrimidine-2-amine (1.3 g) and pyrrolidine (5.2 ml, 62 mmol) to give the title compound (550 mg) as a yellow solid. δH (d⁶ DMSO) 9.57 (1H, s), 8.18 (1H, d, J 5.4 Hz), 7.71 (2H, dd, J 8.8, 5.4 Hz), 7.39 (2H, t, J 8.8 Hz), 7.15 (2H, dd, J 18.6, 2.3 Hz), 6.17 (1H, d, J 5.4 Hz), 4.29 (2H, m), 3.75 (2H,m ), 3.72 (3H, s), 3.66 (3H, s), 3.59 (4H, m), 3.14 (2H, m), 1.98 (2H, m) and 1.89 (2H, m).

The tosylate used as starting material was prepared in a similar manner to the analogous intermediate of Example 21 from N-[4,5-dimethoxy-3-(2-hydroxyethoxy)phenyl]-4-(4-fluorophenylsulphanyl)pyrimidine-2-amine (1.3 g, 3.12 mmol) and p-toluenesulphonyl chloride (1.78 g, 9.35 mmol) to give the desired compound as a light yellow oil which was used without purification.

N-[4,5-Dimethoxy-3-(2-hydroxyethoxy)phenyl]-4-(4-fluorophenylsulphanyl)-pyrimidine-2-amine was prepared by treating a solution of N-(4,5-dimethoxy-3-hydroxyphenyl)-4-(4-fluorophenylsulphanyl)-2-pyrimidineamine (2.23 g, 6.0 mmol) and ethyl carbonate (0.79 g, 9.0 mmol) in dry DMF (25 ml) with potassium carbonate (1.66 h, 12.0 mmol) and heating the resulting mixture at 100° for 16 h. The reaction was concentrated under reduced pressure and the residue partitioned between ethly acetate and water. The aqueous layer was re-extracted with ethyl acetate, the combined organic layers dried (MgSO₄) and evaporated to give a residue which was subjected to column chromatography [silica; 20% hexane-ethyl acetate] to give the desired compound (1.36 g) as a white foam. δH (d⁶ DMSO) 9.48 (1H, s), 8.17 (1H, d, J 5.3 Hz), 7.69 (2H, m), 7.36 (2H, t, J 8.8 Hz), 7.08 (2H, m), 6.15 (1H, d, J 5.3 Hz), 4.81 (1H, t, J 5.2Hz), 3.92 (2H, t, J 5.2 Hz), 3.73 (2H, m), 3.71 (3H, s) and 3.64 (3H, s).

EXAMPLE 28

4-(3-Bromophenylsulphanyl)-N-[4,5-dimethoxy-3-(2-pyrrolidin-1-ylethoxy)phenyl]-2-pyrimidineamine dihydrochloride In a manner analogous to the preparation of the compound of Example 21 from 4-(3-bromophenylsulphanyl)-N-[4,5-dimethoxy-3-(2-p-toluene-sulphonyloxyethoxy)phenyl]-2-pyrimidine-amine (2.16 g) and pyrrolidine (6.2 ml, 75 mmol) to give the title compound (680 mg) as a yellow solid m.p. 154–155°. δH (CDCl₃) 12.0 (1H, br s), 8.25 (1H, br s), 8.03 (1H, d, J 5.7 Hz), 7.73–7.72 (1H, m), 7.62–7.59 (1H, m), 7.53–7.50 (1H, m), 7.33 (1H, t, J 7.9 Hz), 6.87 (2H, s), 6.29 (1H, d, J 5.7 Hz), 4.53–4.47 (2H, br m), 3.90–3.80 (2H, br m), 3.79 (3H, s), 3.77 (3H, s), 3.49–3.42 (2H, br s), 3.08–3.00 (2H, br m), 2.25–2.10 (4H, br m).

The tosylate used as starting material was prepared from 4-(3-bromophenylsulphanyl)-N-[4,5-dimethoxy-3-(2-hydroxyethoxy)phenyl]-2-pyrimidine amine (1.80 g, 3.76 mmol) and p-toluenesulphonyl chloride (2.16 g, 11.3 mmol) in a manner similar to the analogous intermediate of Example 21 and was used without purification.

4-(3-Bromophenylsuphanyl)-N-[4,5-dimethoxy-3-(2-hydroxyethoxyphenyl)-2-pyrimidineamine was prepard in a manner similar to the intermediate of Example 19 as a buff solid. m.p. 151–152°. δH (CDCl₃) 8.07 (1H, d, J 5.4 Hz), 7.75 (1H, t, J 1.8 Hz), 7.61–7.50 (2H, m), 7.31 (1H, t, J 2.4 Hz), 7.17 (1H, br s), 6.87 (1H, d, J 2.4 Hz), 6.86 (1H, d, J 24.4 Hz), 6.25 (1H, d, J 5.4 Hz), 4.08–4.05 (2H, m), 3.91–3.88 (2H, m), 3.81 (3H, s), 3.80 (3H, s) and 2.70 (1H, br s).

EXAMPLE 29

4-(3-Bromophenylsulphanyl)-N-[3-(N'-(S)-1-tert-butoxycarbonylprolyl)aminophenyl]-2-pyrimidineamine In a manner similar to the preparation of the compound of Example 22, from the compound of Example 26 (1.0 g, 2.68 mmol), 1-(3-dimethylaminopropyl)-3-ethyl carbodiimide (514 mg, 2.68 mmol), hydroxyazabenzotriazole (402 mg, 2.95 mmol) N-methylmorpholine (0.88 ml,m 8.04 mmol) and N-tert-butoxycarbonyl)-L-proline (635 mg, 2.95 mmol) to give the title compound (1.34 g) as a white solid m.p. 135–137°. δH (CDCl$_3$) 9.40 (1H, br s), 8.08 (1H, d, J 5.4 Hz), 7.77 (1H, t, J 1.8 Hz), 7.64–7.60 (2H, m), 7.56–7.52 (1H, m), 7.35–7.22 (3H, m), 7.11–7.09 (2H, m), 6.37 (1H, d, J 5.4 Hz), 4.43 (1H, br s), 3.42 (2H, br s), 2.50 (1H, br s), 2.00 (3H, br s) and 1.53 (9H, s).

EXAMPLE 30

4-(3-Bromophenylsulphanyl)-N-[3-(N'-(S)-prolyl) aminophenyl]-2-pyrimidineamine dihydrochloride The compound of Example 29 (1.16, 2.02 mmol) was dissolved in ethyl acetate (100 ml) and dry hydrogen chloride gas was bubbled into the solution. After 10 min a precipitate appeared which was collected and dried to give the title compound (890 mg) as a yellow solid m.p. >175° (decomp). δH (d$^6$ DMSO) 10.73 (1H, s), 10.17 (1H, br m), 9.91 (1H, s), 8.64 (1H, br m), 8.22 (1H, d, J 5.4 Hz), 7.87 (1H, t, J 1.8 Hz), 7.81–7.77 (2H, m), 7.68–7.66 (1H, m), 7.50 (1H, t, J 7.9 Hz), 7.26–7.23 (2H, m), 7.07 (1H, t, J 8.1 Hz), 6.49 (1H, d, J 5.4 Hz), 6.07 (3H, br s), 4.40–4.37 (1H, br m), 3.30–3.20 (2H, br m, 2.43–2.38 (1H, m) and 1.97–1.86 (3H, br m).

EXAMPLE 31

N-{3.5-Dichloro-4-[(2-pyrrolidin-1-yl)ethoxy] phenyl}-4-(3,5-dimethylphenylsulphanyl)-2-pyrimidineamine To a solution of N-(3,5-dichloro-4-hydroxyphenyl)-4-(3, 5-dimethylphenylsulphanyl)-2-pyrimidineamine (1.0 g, 2.55 mmol—prepared from 4-amino-2,6-dichlorophenol and 2-chloro-4-(3,5-dimethylphenylsulphanyl)-pyrimidine according to the method of Example 4) in dry tetrahydrofuran were added triphenylphosphine (802 mg, 3.06 mmol) and N-(2-hydroxyethyl)pyrrolidine (0.3 ml, 2.55 mmol), followed by diethyl azadicarboxylate (0.49 ml, 3.1 mmol). The resulting solution was heated at reflux for 18 h and on cooling the reaction was partitioned between ethyl acetate (200 ml) and saturated aqueous NaHCO$_3$ (200 ml). The organic phase was dried (MgSO$_4$), evaporated and the residue columned (silica; ethyl acetate) to give the title compound (400 mg) as a white foam. δH 8.08 (1H, d, J 5.8 Hz), 7.56 92H, s), 7.17 (2H, s), 7.09 (1H, s), 7.05 (1H, s), 6.28 (1H, d, J 5.8 Hz), 4.18 (2H, t, J 8.6 Hz), 2.59 (2H, t, J 8.6 Hz), 2.59 (2H, t, J 8.6 Hz), 2.69 (4H, m), 2.31 (6H, s) and 1.80 (4H, m). MS m/z 489.2/490.9 (MH+)

BIOLOGICAL ACTIVITY

The following assays were used to demonstrate the activity and selectivity of compounds according to the invention.

The activity of the compounds against src-family protein kinases can be determined in the following two assays:

p56$^{lck}$ Kinase Assay

The tyrosine kinase activity of p56$^{lck}$ was determined using a RR-src peptide (RRLIEDNEYTARG) and [γ-$^{33}$P] ATP as substrates. Quantitation of the $^{33}$P-phosphorylated peptide formed by the action of p56$^{lck}$ was achieved using an adaption of the method of Geissler et al (J. Biol. Chem. (1990) 265, 22255–22261).

All assays were performed in 20 mM HEPES pH 7.5 containing 10 mM MgCl$_2$, 10 mM MnCl$_2$, 0.05% Brij, 1 μM ATP (0.5 μCi[γ-$^{33}$P]ATP) and 0.8 mg/ml RR-src. Inhibitors in dimethylsulphoxide (DMSO) were added such that the final concentration of DMSO did not exceed 1%, and enzyme [human p56$^{lck}$] such that the consumption of ATP was less than 10%. After incubation at 30° C. for 15 min, the reaction was terminated by the addition of one-third volume of stop reagent (0.25 mM EDTA and 33 mM ATP in dH$_2$O). A 15 μl aliquot was removed, spotted onto a P-30 filtermat (Wallac, Milton Keynes, UK), and washed sequentially with 1% acetic acid and dH$_2$O to remove ATP. The bound $^{33}$P-RR-src was quantitated by scintillation counting of the filtermat in a Betaplate scintillation counter (Wallac, Milton Keynes, UK) after addition of Meltilex scintillant (Wallac, Milton Keynes, UK). The dpm obtained, being directly proportional to the amount of $^{33}$P-RR-src produced by p56$^{lck}$, were used to determine the IC$_{50}$ for each compound.

In this assay the most potent compounds according to the invention have IC$_{50}$ values of 100 nM or less.

p59$^{fyn}$ Kinase Assay

Compounds of the invention were assayed for p59$^{fyn}$ inhibitory activity in a similar manner to the p$_{56}^{lck}$ assay, using human p59$^{fyn}$.

The selectivity of compounds according to the invention can be determined in an assay utilising a serine/threonine kinase:

Protein Kinase C Assay

Inhibitor activity against protein kinase C (PKC) was determined using PKC obtained from Sigma Chemical Company (Poole, UK) and a commercially available assay system (Amersham International plc, Little Chalfont, UK). Briefly, PKC catalyses the transfer of the γ-phosphate ($^{32}$p) of ATP to the threonine group on a peptide specific for PKC. Phosphorylated peptide is bound go phosphocellulse paper, subsequently quantified by scintillation counting and IC$_{50}$ values determined as described above.

In this assay, compounds according to the invention have IC$_{50}$ values of 1 μm and above.

What is claimed is:
1. A compound of formula (1)

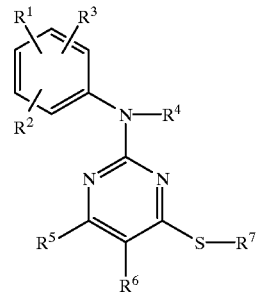

(1)

wherein:
R$^1$ is an —XR$^8$, —NO$_2$, —CN, —SO$_2$N(R$^8$)$_2$, —CON (R$^8$)$_2$, —CSN(R$^8$)$_2$, —NH$_2$, —NR$^9$R$^{10}$, —N(R$^{10}$) COR$^9$, —N(R$^{10}$)CSR$^9$, —N(R$^{10}$)SOR$^9$, —N(R$^{10}$) SO$_2$R$^9$, —N(R$^{10}$)CONH$_2$, —N(R$^{10}$)CONR$^9$R$^{10}$, —N(R$^{10}$)C(O)OR$^9$, —N(R$^{10}$)C(NH)NH$_2$, —N(R$^{10}$) C(NH)NR$^9$R$^{10}$, —N(R$^{10}$)CSNH$_2$, —N(R$^{10}$) CSNR$^9$R$^{10}$, —N(R$^{10}$)SONH$_2$, —N(R$^{10}$)SONR$^9$R$^{10}$, —N(R$^{10}$)SO$_2$NH$_2$, —N(R$^{10}$)SO$_2$NR$^9$R$^{10}$ or —N(R$^{10}$)Cyc$^1$ group;

$R^2$ and $R^3$, which may be the same or different, is each a hydrogen or halogen atom or a group selected from an optionally substituted $C_{1-10}$aliphatic group optionally interrupted with one to four $X^2$ heteroatoms or groups, an optionally substituted $C_{3-10}$cycloaliphatic group optionally containing one to four heteroatoms or groups $X^2$ groups, $-OR^{10}$, $-OR^{10a}$, $-NO_2$, $-CN$, $-SR^8$, $-COR^8$, $-S(O)R^8$, $-SO_2R^8$, $-SO_2N(R^8)_2$, $-CO_2R^8$, $-CON(R^8)_2$, $-CSN(R^8)_2$, $-NH_2$, $-NR^9R^{10}$, $-N(R^{10})COR^9$, $-N(R^{10})CSR^9$, $-N(R^{10})SOR^9$, $-N(R^{10})SO_2R^9$, $-N(R^{10})CONH_2$, $-N(R^{10})CONR^9R^{10}$, $-N(R^{10})C(O)OR^9$, $-N(R^{10})C(NH)NH_2$, $-N(R^{10})C(NH)NR^9R^{10}$, $-N(R^{10})CSNH_2$, $-N(R^{10})CSNR^9R^{10}$, $-N(R^{10})SONH_2$, $-N(R^{10})SONR^9R^{10}$, $-N(R^{10})SO_2NH_2$, $-N(R^{10})SO_2NR^9R^{10}$ or $-N(R^{10})Cyc^1$ group;

$R^4$ is a hydrogen atom or a straight or branched chain $C_{1-6}$alkyl group;

$R^5$ is a hydrogen atom or an optionally substituted straight or branched chain $C_{1-6}$alkyl, $C_{2-6}$alkenyl or $C_{2-6}$alkynyl group;

$R^6$ is a hydrogen or halogen atom or an $-NO_2$, $-CO_2R^8$, $-NH_2$, $-NR^9R^{10}$, $-N(R^{10})COR^9$, $-N(R^{10})CSR^9$, $-N(R^{10})SOR^9$, $-N(R^{10})SO_2R^9$, $-N(R^{10})CONH_2$, $-N(R^{10})CONR^9R^{10}$, $-N(R^{10})C(O)OR^9$, $-N(R^{10})C(NH(NH)NH_2$, $-N(R^{10})CNR^9R^{10}$, $-N(R^{10})CSNH_2$, $-N(R^{10})CSNR^9R^{10}$, $-N(R^{10})SONH_2$, $-N(R^{10})SONR^9R^{10}$, $-N(R^{10})SO_2NH_2$, $-N(R^{10})SO_2NR^9R^{10}$, $-N(R^{10})Cyc^1$ or $-X^1R^{6a}$ group;

$R^{6a}$ is an optionally substituted straight or branched chain $C_{1-6}$alkyl, $C_{2-6}$alkenyl or $C_{2-6}$alkynyl group;

$R^7$ is an optionally substituted $C_{1-10}$aliphatic group optionally interrupted with one to four heteroatoms or groups $X^2$, an optionally substituted $C_{3-10}$cycloaliphatic group optionally containing one to four heteroatoms or groups $X^2$, an optionally substituted monocyclic or bicyclic $C_{6-12}$aryl group or an optionally substituted monocyclic or bicyclic $C_{1-9}$heteroaryl group containing one to four heteroatoms selected from oxygen, sulfur or nitrogen atoms;

each $R^8$ is independently a hydrogen atom or an optionally substituted $C_{1-10}$aliphatic group optionally interrupted with one to four heteroatoms or groups $X^2$, an optionally substituted $C_{3-10}$cycloaliphatic group optionally containing one to four heteroatoms or groups $X^2$, an optionally substituted monocyclic or bicyclic $C_{6-12}$aryl group or an optionally substituted monocyclic or bicyclic $C_{1-9}$heteroaryl group containing one to four heteroatoms selected from oxygen, sulfur or nitrogen atoms;

$R^9$ is an optionally substituted straight or branched chain $C_{1-6}$alkyl, $C_{2-6}$alkenyl or $C_{2-6}$alkynyl group, each of which is optionally interrupted with one or two heteroatoms or groups $X^3$;

$R^{10}$ is a hydrogen atom or an optionally substituted straight or branched chain $C_{1-6}$alkyl, $C_{2-6}$alkenyl or $C_{2-6}$alkynyl group, each of which is optionally interrupted with one to four heteroatoms or groups $X^3$;

$R^{10a}$ is an optionally substituted $C_{1-10}$aliphatic group optionally interrupted with one to four heteroatoms or groups $X^2$, an optionally substituted $C_{3-10}$cycloaliphatic group optionally containing one to four heteroatoms or groups $X^2$, an optionally substituted monocyclic or bicyclic $C_{6-12}$aryl group or an optionally substituted monocyclic or bicyclic $C_{1-9}$heteroaryl group containing one to four heteroatoms selected from oxygen, sulfur or nitrogen atoms;

X is a direct bond or a linker atom or group selected from $-O-$, $-S-$, $-C(O)-$, $-C(S)-$, $-C(O)O-$, $-S(O)-$, $-S(O)_2-$, $-CH_2-$ or $-N(R^{9a})-$, where $R^{9a}$ is a hydrogen atom or a straight or branched chain $C_{1-6}$alkyl group;

$X^1$ is a direct bond or a linker atom or group selected from $-O-$, $-S-$, $-C(O)-$, $-C(S)-$, $-S(O)-$, $-S(O)_2-$, $-N(R^{11})-$, $-CON(R^{11})-$, $-OC(O)N(R^{11})-$, $-CSN(R^{11})-$, $-N(R^{11})CO-$, $-N(R^{11})C(O)O-$, $-N(R^{11})CS-$, $-SON(R^{11})-$, $-SO_2N(R^{11})-$, $-N(R^{11})SO_2-$, $-N(R^{11})CON(R^{11})-$, $-N(R^{11})CSN(R^{11})-$, $-N(R^{11})SON(R^{11})-$ and $-N(R^{11})SO_2N(R^{11})-$;

$R^{11}$ is a hydrogen atom or a $C_{1-6}$ alkyl group;

$X^2$ and $X^3$, which may be the same or different, is each a linker atom or group selected from $-O-$, $-S-$, $-C(O)-$, $-C(S)-$, $-S(O)$, $-S(O)_2-$, $-N(R^{11})-$, $-CON(R^{11})-$, $-OC(O)N(R^{11})-$, $-CSN(R^{11})-$, $-N(R^{11})CO-$, $-N(R^{11})C(O)O-$, $-N(R^{11})CS-$, $-SON(R^{11})-$, $-SO_2N(R^{11})-$, $-N(R^{11})SO_2-$, $-N(R^{11})CON(R^{11})-$, $-N(R^{11})CSN(R^{11})-$, $-N(R^{11})SON(R^{11})-$ and $-N(R^{11})SO_2N(R^{11})-$;

wherein said optional substituents on said alkyl, alkenyl, alkynyl, aliphatic, heteroaliphatic, cycloaliphatic and heterocycloaliphatic groups in $R^2$, $R^3$, $R^5$, $R^{6a}$, $R^7$, $R^8$, $R^9$, $R^{10}$ and $R^{10a}$ are one or more groups selected from halogen, hydroxyl, $C_{1-6}$alkoxy, thiol, $C_{1-6}$alkylthio, $-SC(NH)NH_2$, $-CH_2SC(NH)NH_2$, $NH_2$, $-NR^9R^{10}$, and $C_{3-7}$cyclic amino which is optionally substituted with one to three halogen atoms or $C_{1-4}$alkyl, hydroxyl or $C_{1-4}$alkoxy groups and which optionally contains one or more other heteroatoms or heteroatom containing groups selected from $-O-$, $-S-$, $-C(O)-$, $-C(S)-$, $-S(O)-$ or $-S(O)_2-$;

wherein said optional substituents on said aryl and heteroaryl groups in $R^7$, $R^8$ and $R^{10a}$ are one or more $R^{12}$ groups, where $R^{12}$ is $R^{13}$ or $-Alk(R^{13})_m$;

$R^{13}$ is a halogen atom, $-NH_2$, $-NHR^{14}$, $-N(R^{14})_2$, $-NO_2$, $-CN$, $-OH$, $-OR^{14}$, $-CHO$, $-CO_2H$, $-CO_2Alk^1$, $-SH$, $SR^{14}$, $-COR^{14}$, $-CSR^{14}$, $-SO_3H$, $-SO_2R^{14}$, $-SO_2NH_2$, $-SO_2NHR^{14}$, $-SO_2N(R^{14})_2$, $-CONH_2$, $-CSNH_2$, $-CONHR^{14}$, $-CSNHR^{14}$, $-CON(R^{14})_2$, $-CSN(R^{14})_2$, $-N(R^{11})SO_2H$, $-N(R^{11})SO_2R^{14}$, $-N(SO_2R^{14})_2$, $-N(R^{11})SO_2NH_2$, $-N(R^{11})SO_2NHR^{14}$, $-N(R^{11})SO_2N(R^{14})_2$, $-N(R^{11})COR^{14}$, $-N(R^{11})CONH_2$, $-N(R^{11})CONHR^{14}$, $-N(R^{11})CON(R^{14})_2$, $-N(R^{11})CSR^{14}$, $-N(R^{11})CSNH_2$, $-N(R^{11})CSNHR^{14}$, $-N(R^{11})CSN(R^{14})_2$, $-N(R^{11})C(O)OR^{14}$, optionally substituted $C_{5-7}$cycloalkyl, optionally substituted monocyclic or bicyclic $C_{6-12}$aryl or optionally substituted monocyclic or bicyclic $C_{5-13}$heteroaryl, wherein said cycloalkyl, aryl and heteroaryl substituents are one or two groups selected from $C_{1-6}$alkyl, hydroxyl ($-OH$), hydroxy$C_{1-6}$alkyl and $C_{1-6}$alkyoxy groups;

$R^{14}$ is $-Alk(R^3)_m$, hetero$C_{3-6}$cycloalkyl, $-Alk$-hetero$C_{3-6}$cycloalkyl, monocyclic or bicyclic $C_{6-12}$aryl or monocyclic or bicyclic $C_{1-9}$heteroaryl;

Alk is a straight or branched chain $C_{1-6}$alkylene, $C_{2-6}$alkenylene or $C_{2-6}$alkynylene group optionally interrupted by one, two or three $-O-$ or $-S-$atoms or $-SO-$, $-S(O)_2-$ or $-N(R^{11})-$ groups;

$Alk^1$ is a straight or branched chain $C_{1-8}$alkyl group which is optionally substituted with one or more $R^{13}$ groups;

Cyc¹ is a optionally substituted $C_{3-7}$monocyclic carbocyclic group optionally containing one or more —O— or —S— atoms or —C(O)—, —C(S)—, —SO—, —S(O)$_2$— or —N(R$^{11}$)— groups, wherein said optional Cyc¹ substituents are selected from one to three halogen atoms or $C_{1-4}$alkyl, hydroxy or $C_{1-4}$alkoxy groups;

m is zero or an integer 1, 2 or 3;

and the salts, solvates, hydrates and N-oxides thereof; with the provisos that:

(1) when one or both of R² and R³ is an —OR¹⁰ group, then R¹ is an —OR⁸ group in which R⁸ is an optionally substituted $C_{1-10}$aliphatic group substituted by a cyclic amino group, an optionally substituted $C_{1-10}$aliphatic group interrupted with one to four atoms or groups X², an optionally substituted $C_{3-10}$cycloaliphatic group optionally containing one to four atoms or groups X², an optionally substituted monocyclic or bicyclic $C_{6-12}$aryl group or an optionally substituted monocyclic or bicyclic $C_{1-9}$heteroaryl group containing one to four heteroatoms selected from oxygen, sulfur or nitrogen atoms;

(2) when R⁵ is a $C_{1-6}$alkyl or trifluoromethyl group and R⁷ is a $C_{1-6}$alkyl group optionally substituted with cyano or alkoxy or a $C_{2-6}$alkenyl, $C_{2-6}$alkynyl or —CH$_2$Ar group where Ar is phenyl, then at least one of R¹, R², R³, R⁴ and R⁶ is other than a hydrogen atom;

(3) when one of R¹, R² and R³ is bromo, chloro, fluoro, trifluoromethyl, methyl, methoxy, isopropoxy, or trifluoromethoxy and the other of R¹, R² and R³ are hydrogen, chloro, fluoro, methyl or trifluoromethyl, R⁴ and R⁶ are hydrogen and R⁷ is methyl, ethyl, propyl or butyl, then R⁵ is other than trifluoromethyl; and (4) when R⁴ and R⁶ are hydrogen, R⁵ is hydrogen or methyl and R⁷ is ethyl, propyl, butyl or —CH$_2$Ar where Ar is phenyl, then at least two of R¹, R² and R³ are other than nitro groups.

2. A compound according to claim 1 in which R⁴, R⁵ and R⁶ is each a hydrogen atom.

3. A compound according to claim 1 in which R⁷ is an optionally substituted monocyclic or bicyclic $C_{6-12}$aryl group or an optionally substituted monocyclic or bicyclic $C_{1-9}$heteroaryl group containing one to four heteroatoms selected from oxygen, sulfur or nitrogen atoms.

4. A compound according to claim 3 in which R⁷ is an optionally substituted phenyl, 1- or 2-naphthyl, pyrrolyl, furyl, thienyl, indolyl, pyrazolyl, thiazolyl, [2,3-dihydro]benzofuryl, benzothiazolyl, 2-pyridyl, 3-pyridyl or 4-pyridyl group.

5. A compound according to claim 1 in which R¹ is attached at the 3- position of the phenyl ring R² and R³ are attached at the 4- and 5-positions or R¹ is attached at the 4-position and R² and R³ are attached at the 3- and 5-positions.

6. A compound according to claim 5 in which R¹ is a —R⁸ or —OR⁸ group.

7. A compound according to claim 6 in which R¹ is an optionally substituted $C_{3-10}$cycloaliphatic group containing one to four X² groups or an alkoxy group.

8. A compound according to claim 5 in which R² or R³ is each a hydrogen atom or a methyl or methoxy group.

9. A pharmaceutical composition comprising a compound of formula (1)

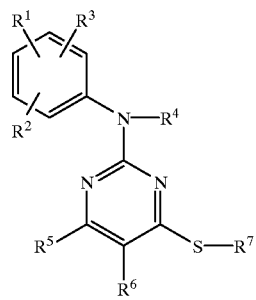

wherein:

R¹ is an —XR⁸, —NO$_2$, —CN, —SO$_2$N(R⁸)$_2$, —CON(R⁸)$_2$, —CSN(R⁸), —NH$_2$, —NR⁹R¹⁰, —N(R¹⁰)COR⁹, —N(R¹⁰)CSR⁹, —N(R¹⁰)SOR⁹, —N(R¹⁰)SO$_2$R⁹, —N(R¹⁰)CONH$_2$, —N(R¹⁰)CONR⁹R¹⁰, —N(R¹⁰)C(O)OR⁹, —N(R¹⁰)C(NH)NH$_2$, —N(R¹⁰)C(NH)NR⁹R¹⁰, —N(R¹⁰)CSNH$_2$, —N(R¹⁰)CSNR⁹R¹⁰, —N(R¹⁰)SONH$_2$, —N(R¹⁰)SONR⁹R¹⁰, —N(R¹⁰)SO$_2$NH$_2$, —N(R¹⁰)SO$_2$NR⁹R¹⁰ or —N(R¹⁰)Cyc¹ group;

R² and R³, which may be the same or different, is each a hydrogen or halogen atom or a group selected from an optionally substituted $C_{1-10}$aliphatic group optionally interrupted with one to four X² heteroatoms or groups, an optionally substituted $C_{3-10}$cycloaliphatic group optionally containing one to four heteroatoms or groups X² groups, —OR¹⁰, —OR¹⁰ᵃ, —NO$_2$, —CN, —SR⁸, —COR⁸, —S(O)R⁸, —SO$_2$R⁸, —SO$_2$N(R⁸)$_2$, —CO$_2$R⁸, —CON(R⁸)$_2$, —CSN(R⁸)$_2$, —NH$_2$, —NR⁹R¹⁰, —N(R¹⁰)COR⁹, —N(R¹⁰)CSR⁹, —N(R¹⁰)SOR⁹, —N(R¹⁰)SO$_2$R⁹, —N(R¹⁰)CONH$_2$, —N(R¹⁰)CONR⁹R¹⁰, —N(R¹⁰)C(O)OR⁹, —N(R¹⁰)C(NH)NH$_2$, —N(R¹⁰)C(NH)NR⁹R¹⁰, —N(R¹⁰)CSNH$_2$, —N(R¹⁰)CSNR⁹R¹⁰, —N(R¹⁰)SONH$_2$, —N(R¹⁰)SONR⁹R¹⁰, —N(R¹⁰)SO$_2$, NH$_2$, —N(R¹⁰)SO$_2$NR⁹R¹⁰ or —N(R¹⁰)Cyc¹ group;

R⁴ is a hydrogen atom or a straight or branched chain $C_{1-6}$alkyl group;

R⁵ is a hydrogen atom or an optionally substituted straight or branched chain $C_{1-6}$alkyl, $C_{2-6}$alkenyl or $C_{2-6}$alkynyl group;

R⁶ is a hydrogen or halogen atom or an —NO$_2$, —CO$_2$R⁸, —NH$_2$, —NR⁹R¹⁰, —N(R¹⁰)COR⁹, —N(R¹⁰)CSR⁹, —N(R¹⁰)SOR⁹, —N(R¹⁰)SO$_2$R⁹, —N(R¹⁰)CONH$_2$, —N(R¹⁰)CONR⁹R¹⁰, —N(R¹⁰)C(O)OR⁹, —N(R¹⁰)C(NH)NH$_2$, —N(R¹⁰)C(NH)NR⁹R¹⁰, —N(R¹⁰))CSNH$_2$, —N(R¹⁰)CSNR⁹R¹⁰, —N(R¹⁰)SONH$_2$, —N(R¹⁰)SONR⁹R¹⁰, —N(R¹⁰)SO$_2$NH$_2$, —N(R¹⁰)SO$_2$NR⁹R¹⁰, —N(R¹⁰)Cyc¹ or X¹R⁶ᵃ group;

R⁶ᵃ is an optionally substituted straight or branched chain $C_{1-6}$alkyl, $C_{2-6}$alkenyl or $C_{2-6}$alkynyl group;

R⁷ is an optionally substituted $C_{1-10}$aliphatic group optionally interrupted with one to four heteroatoms or groups X², an optionally substituted $C_{3-10}$cycloaliphatic group optionally containing one to four heteroatoms or groups X², an optionally substituted monocyclic or bicyclic $C_{6-12}$aryl group or an optionally substituted monocyclic or bicyclic $C_{1-9}$ heteroaryl group containing one to four heteroatoms selected from oxygen, sulfur or nitrogen atoms;

each $R^8$ is independently a hydrogen atom or an optionally substituted $C_{1-10}$aliphatic group optionally interrupted with one to four heteroatoms or groups $X^2$, an optionally substituted $C_{3-10}$cycloaliphatic group optionally containing one to four heteroatoms or groups $X^2$, an optionally substituted monocyclic or bicyclic $C_{6-12}$aryl group or an optionally substituted monocyclic or bicyclic $C_{1-9}$heteroaryl group containing one to four heteroatoms selected from oxygen, sulfur or nitrogen atoms;

$R^9$ is an optionally substituted straight or branched chain $C_{1-6}$alkyl, $C_{2-6}$alkenyl or $C_{2-6}$alkynyl group, each of which is optionally interrupted with one or two heteroatoms or groups $X^3$;

$R^{10}$ is a hydrogen atom or an optionally substituted straight or branched chain $C_{1-6}$alkyl, $C_{2-6}$alkenyl or $C_{2-6}$alkynyl group, each of which is optionally interrupted with one to four heteroatoms or groups $X^3$;

$R^{10a}$ is an optionally substituted $C_{1-10}$aliphatic group optionally interrupted with one to four heteroatoms or groups $X^2$, an optionally substituted $C_{3-10}$cycloaliphatic group optionally containing one to four heteroatoms or groups $X^2$, an optionally substituted monocyclic or bicyclic $C_{6-12}$aryl group or an optionally substituted monocyclic or bicyclic $C_{1-9}$heteroaryl group containing one to four heteroatoms selected from oxygen, sulfur or nitrogen atoms;

X is a direct bond or a linker atom or group selected from —O—, —S—, —C(O)—, —C(S)—, —C(O)O—, —S(O)—, —S(O)$_2$—, —CH$_2$— or —N($R^{9a}$)—, where $R^{9a}$ is a hydrogen atom or a straight or branched chain $C_{1-6}$alkyl group;

$X^1$ is a direct bond or a linker atom or group selected from —O—, —S—, —C(O)—, —C(S)—, —S(O)—, —S(O)$_2$—, —N($R^{11}$)—, —CON($R^{11}$)—, —OC(O)N($R^{11}$)—, —CSN($R^{11}$)—, —N($R^{11}$)CO—, —N($R^{11}$)C(O)O—, —N($R^{11}$)CS—, —SON($R^{11}$)—, —SO$_2$N($R^{11}$)—, —N($R^{11}$)SO$_2$—, —N($R^{11}$)CON($R^{11}$)—, —N($R^{11}$)CSN($R^{11}$)—, —N($R^{11}$)SON($R^{11}$)— and —N($R^{11}$)SO$_2$N($R^{11}$)—;

$R^{11}$ is a hydrogen atom or a $C_{1-6}$alkyl group;

$X^2$ and $X^3$, which may be the same or different, is each a linker atom or group selected from —O—, —S—, —C(O)—, —C(S)—, —S(O)—, —S(O)$_2$—, —N($R^{11}$)—, —CON($R^{11}$)—, —OC(O)N($R^{11}$)—, —CSN($R^{11}$), —N($R^{11}$)CO—, —N($R^{11}$)C(O)O—, —N($R^{11}$)CS—, —SON($R^{11}$)—, —SO$_2$N($R^{11}$)—, —N($R^{11}$)SO$_2$—, —N($R^{11}$)CON($R^{11}$), —N($R^{11}$)CSN($R^{11}$)—, —N($R^{11}$)SON($R^{11}$)— and —N($R^{11}$)SO$_2$N($R^{11}$)—;

wherein said optional substituents on said alkyl, alkenyl, alkynyl, aliphatic, heteroaliphatic, cycloaliphatic and heterocycloaliphatic groups in $R^2$, $R^3$, $R^5$, $R^{6a}$, $R^7$, $R^8$, $R^9$, $R^{10}$ and $R^{10a}$ are one or more groups selected from halogen, hydroxyl, $C_{1-6}$alkoxy, thiol, $C_{1-6}$alkylthio, —SC(NH)NH$_2$, —CH$_2$SC(NH)NH$_2$, NH$_2$, —NR$^9$R$^{10}$, and $C_{3-7}$cyclic amino which is optionally substituted with one to three halogen atoms or $C_{1-4}$alkyl, hydroxyl or $C_{1-4}$alkoxy groups and which optionally contains one or more other heteroatoms or heteroatom containing groups selected from —O—, —S—, —C(O)—, —C(S)—, —S(O)— or —S(O)$_2$—;

wherein said optional substituents on said aryl and heteroaryl groups in $R^7$, $R^8$ and $R^{10a}$ are one or more $R^{12}$ groups, where $R^{12}$ is $R^{13}$ or —Alk($R^{13}$)$_m$;

$R^{13}$ is a halogen atom, —NH$_2$, NHR$^{14}$, —N(R$^{14}$)$_2$, —NO$_2$, —CN, —OH, —OR$^{14}$, —CHO, —CO$_2$H, —CO$_2$Alk$^1$, —SH, SR$^{14}$, —COR$^{14}$, —CSR$^{14}$, —SO$_3$H, —SO$_2$R$^{14}$, —SO$_2$NH$_2$, —SO$_2$NHR$^{14}$, —SO$_2$N(R$^{14}$)$_2$, —CONH$_2$, —CSNH$_2$, —CONHR$^{14}$, —CSNHR$^{14}$, —CON(R$^{14}$)$_2$, —CSN(R$^{14}$)$_2$, —N(R$^{11}$)SO$_2$H, —N(R$^{11}$)SO$_2$R$^{14}$, —N(SO$_2$R$^{14}$)$_2$, —N(R$^{11}$)SO$_2$NH$_2$, —N(R$^{11}$)SO$_2$NHR$^{14}$, —N(R$^{11}$)SO$_2$N(R$^{14}$)$_2$, —N(R$^{11}$)COR$^{14}$, —N(R$^{11}$)CONH$_2$, —N(R$^{11}$)CONHR$^{14}$, —N(R$^{11}$)CON(R$^{14}$)$_2$, —N(R$^{11}$)CSR$^{14}$, —N(R$^{11}$)CSNH$_2$, —N(R$^{11}$)CSNHR$^{14}$, —N(R$^{11}$)CSN(R$^{14}$)$_2$, —N(R$^{11}$)C(O)OR$^{14}$, optionally substituted $C_{5-7}$cycloalkyl, optionally substituted monocyclic or bicyclic $C_{6-12}$aryl or optionally substituted monocyclic or bicyclic $C_{5-13}$heteroaryl, wherein said cycloalkyl, aryl and heteroaryl substituents are one or two groups selected from $C_{1-6}$alkyl, hydroxyl (—OH), hydroxy$C_{1-6}$alkyl and $C_{1-6}$alkyoxy groups;

$R^{14}$ is —Alk($R^{13}$)$_m$, heteroC$_{3-6}$cycloalkyl, —Alk-heteroC$_{3-6}$cycloalkyl, monocyclic or bicyclic $C_{6-12}$aryl or monocyclic or bicyclic $C_{1-9}$heteroaryl;

Alk is a straight or branched chain $C_{1-6}$alkylene, $C_{2-6}$alkenylene or $C_{2-6}$alkynylene group optionally interrupted by one, two or three —O— or —S— atoms or —SO—, —S(O)$_2$— or —N(R$^{11}$)— groups;

Alk$^1$ is a straight or branched chain $C_{1-8}$alkyl group which is optionally substituted with one or more $R^{13}$ groups;

Cyc$^1$ is a optionally substituted $C_{3-7}$ monocyclic carbocyclic group optionally containing one or more —O— or —S— atoms or —C(O)—, —C(S)—, —SO—, —S(O)$_2$— or —N(R$^{11}$)— groups, wherein said optional Cyc$^1$ substituents are selected from one to three halogen atoms or $C_{1-4}$alkyl, hydroxy or $C_{1-4}$alkoxy groups;

m is zero or an integer 1, 2 or 3;

and the salts, solvates, hydrates and N-oxides thereof; with the provisos that:

(1) when one or both of $R^2$ and $R^3$ is an —OR$^{10}$ group, then $R^1$ is an —OR$^8$ group in which $R^8$ is an optionally substituted $C_{1-10}$aliphatic group substituted by a cyclic amino group, an optionally substituted $C_{1-10}$aliphatic group interrupted with one to four atoms or groups $X^2$, an optionally substituted $C_{3-10}$cycloaliphatic group optionally containing one to four atoms or groups $X^2$, an optionally substituted monocyclic or bicyclic $C_{6-12}$aryl group or an optionally substituted monocyclic or bicyclic $C_{1-9}$heteroaryl group containing one to four heteroatoms selected from oxygen, sulfur or nitrogen atoms;

(2) when $R^5$ is a $C_{1-6}$alkyl or trifluoromethyl group and $R^7$ is a $C_{1-6}$alkyl group optionally substituted with cyano or alkoxy or a $C_{2-6}$alkenyl, $C_{2-6}$alkynyl or —CH$_2$Ar group where Ar is phenyl, then at least one of $R^1$, $R^2$, $R^3$, $R^4$ and $R^6$ is other than a hydrogen atom;

(3) when one of $R^1$, $R^2$ and $R^3$ is bromo, chloro, fluoro, trifluoromethyl, methyl, methoxy, isopropoxy, or trifluoromethoxy and the other of $R^1$, $R^2$ and $R^3$ are hydrogen, chloro, fluoro, methyl or trifluoromethyl, $R^4$ and $R^6$ are hydrogen and $R^7$ is methyl, ethyl, propyl or butyl, then $R^5$ is other than trifluoromethyl; and (4) when $R^4$ and $R^6$ are hydrogen, $R^5$ is hydrogen or methyl and $R^7$ is ethyl, propyl, butyl or —CH$_2$Ar where Ar is phenyl, then at least two of $R^1$, $R^2$ and $R^3$ are other than nitro groups;

together with one or more pharmaceutically acceptable carriers, excipients or diluents.

10. A method for the prophylaxis or treatment of a disease or disorder in a mammal in which inappropriate protein tyrosine kinase action plays a role, which comprises administering to a mammal suffering from such a disease or disorder a therapeutically effective amount of a compound of formula (1)

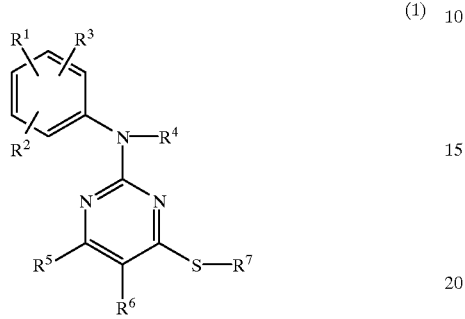

wherein:

$R^1$ is an —$XR^8$, —$NO_2$, —CN, —$SO_2N(R^8)_2$, —$CON(R^8)_2$, —$CSN(R^8)_2$, —$NH_2$, —$NR^9R^{10}$, —$N(R^{10})COR^9$, —$N(R^{10})CSR^9$, —$N(R^{10})SOR^9$, —$N(R^{10})SO_2R^9$, —$N(R^{10})CONH_2$, —$N(R^{10})CONR^9R^{10}$, —$N(R^{10})C(O)OR^9$, —$N(R^{10})C(NH)NH_2$, —$N(R^{10})C(NH)NR^9R^{10}$, —$N(R^{10})CSNH_2$, —$N(R^{10})CSNR^9R^{10}$, —$N(R^{10})SONH_2$, —$N(R^{10})SONR^9R^{10}$, —$N(R^{10})SO_2NH_2$, —$N(R^{10})SO_2NR^9R^{10}$ or —$N(R^{10})Cyc^1$ group;

$R^2$ and $R^3$, which may be the same or different, is each a hydrogen or halogen atom or a group selected from an optionally substituted $C_{1-10}$aliphatic group optionally interrupted with one to four $X^2$ heteroatoms or groups, an optionally substituted $C_{3-10}$cycloaliphatic group optionally containing one to four heteroatoms or groups $X^2$ groups, —$OR^{10}$, —$OR^{10a}$, —$NO_2$, —CN, —$SR^8$, —$COR^8$, —$S(O)R^8$, —$SO_2R^8$, —$SO_2N(R^8)_2$, —$CO_2R^8$, —$CON(R^8)_2$, —$CSN(R^8)_2$, —$NH_2$, —$NR^9R^{10}$, —$N(R^{10})COR^9$, —$N(R^{10})CSR^9$, —$N(R^{10})SOR^9$, —$N(R^{10})SO_2R^9$, —$N(R^{10})CONH_2$, —$N(R^{10})CONR^9R^{10}$, —$N(R^{10})C(O)OR^9$, —$N(R^{10})C(NH)NH_2$, —$N(R^{10})C(NH)NR^9R^{10}$, —$N(R^{10})CSNH_2$, —$N(R^{10})CSNR^9R^{10}$, —$N(R^{10})SONH_2$, —$N(R^{10})SONR^9R^{10}$, —$N(R^{10})SO_2NH_2$, —$N(R^{10})SO_2NR^9R^{10}$ or —$N(R^{10})Cyc^1$ group;

$R^4$ is a hydrogen atom or a straight or branched chain $C_{1-6}$alkyl group;

$R^5$ is a hydrogen atom or an optionally substituted straight or branched chain $C_{1-6}$alkyl, $C_{2-6}$alkenyl or $C_{2-6}$alkynyl group;

$R^6$ is a hydrogen or halogen atom or an —$NO_2$, —$CO_2R^8$, —$NH_2$, —$NR^9R^{10}$, —$N(R^{10})COR^9$, —$N(R^{10})CSR^9$, —$N(R^{10})SOR^9$, —$N(R^{10})SO_2R^9$, —$N(R^{10})CONH_2$, —$N(R^{10})CONR^9R^{10}$, —$N(R^{10})C(O)OR^9$, —$N(R^{10})C(NH)NH_2$, —$N(R^{10})C(NH)NR^9R^{10}$, —$N(R^{10})CSNH_2$, —$N(R^{10})CSNR^9R^{10}$, —$N(R^{10})SONH_2$, —$N(R^{10})SONR^9R^{10}$, —$N(R^{10})SO_2NH_2$, —$N(R^{10})SO_2NR^9R^{10}$, —$N(R^{10})Cyc^1$ or —$X^1R^{6a}$ group;

$R^{6a}$ is an optionally substituted straight or branched chain $C_{1-6}$alkyl, $C_{2-6}$alkenyl or $C_{2-6}$alkynyl group;

$R^7$ is an optionally substituted $C_{1-10}$aliphatic group optionally interrupted with one to four heteroatoms or groups $X^2$, an optionally substituted $C_{3-10}$cycloaliphatic group optionally containing one to four heteroatoms or groups $X^2$, an optionally substituted monocyclic or bicyclic $C_{6-12}$aryl group or an optionally substituted monocyclic or bicyclic $C_{1-9}$heteroaryl group containing one to four heteroatoms selected from oxygen, sulfur or nitrogen atoms;

each $R^8$ is independently a hydrogen atom or an optionally substituted $C_{1-10}$aliphatic group optionally interrupted with one to four heteroatoms or groups $X^2$, an optionally substituted $C_{3-10}$cycloaliphatic group optionally containing one to four heteroatoms or groups $X^2$, an optionally substituted monocyclic or bicyclic $C_{6-12}$aryl group or an optionally substituted monocyclic or bicyclic $C_{1-9}$heteroaryl group containing one to four heteroatoms selected from oxygen, sulfur or nitrogen atoms;

$R^9$ is an optionally substituted straight or branched chain $C_{1-6}$alkyl, $C_{2-6}$alkenyl or $C_{2-6}$alkynyl group, each of which is optionally interrupted with one or two heteroatoms or groups $X^3$;

$R^{10}$ is a hydrogen atom or an optionally substituted straight or branched chain $C_{1-6}$allyl, $C_{2-6}$alkenyl or $C_{2-6}$alkynyl group, each of which is optionally interrupted with one to four heteroatoms or groups $X^3$;

$R^{10a}$ is an optionally substituted $C_{1-10}$aliphatic group optionally interrupted with one to four heteroatoms or groups $X^2$, an optionally substituted $C_{3-10}$cycloaliphatic group optionally containing one to four heteroatoms or groups $X^2$, an optionally substituted monocyclic or bicyclic $C_{6-12}$aryl group or an optionally substituted monocyclic or bicyclic $C_{1-9}$heteroaryl group containing one to four heteroatoms selected from oxygen, sulfur or nitrogen atoms;

X is a direct bond or a linker atom or group selected from —O—, —S—, —C(O)—, —C(S)—, —C(O)O—, —S(O)—, —$S(O)_2$—, —$CH_2$— or —$N(R^{9a})$, where $R^{9a}$ is a hydrogen atom or a straight or branched chain $C_{1-6}$alkyl group;

$X^1$ is a direct bond or a linker atom or group selected from —O—, —S—, —C(O)—, —C(S)—, —S(O)—, —$S(O)_2$—, —$N(R^{11})$—, —$CON(^{11})$—, —$OC(O)N(R^{11})$—, —$CSN(R^{11})$—, —$N(R^{11})CO$—, —$N(R^{11})C(O)O$—, —$N(R^{11})CS$—, —$SON(R^{11})$—, —$SO_2N(R^{11})$—, —$N(R^{11})SO_2$—, —$N(R^{11})CON(R^{11})$—, —$N(R^{11})CSN(R^{11})$—, —$N(R^{11})SON(R^{11})$— and —$N(R^{11})SO_2N(R^{11})$—;

$R^{11}$ as a hydrogen atom or a $C_{1-6}$alkyl group;

$X^2$ and $X^3$, which may be the same or different, is each a linker atom or group selected from —O—, —S—, —C(O)—, —C(S)—, —S(O)—, —$S(O)_2$—, —$N(R^{11})$—, —$CON(R^{11})$—, —$OC(O)N(R^{11})$—, —$CSN(R^{11})$—, —$N(R^{11})CO$—, —$N(R^{11})C(O)O$—, —$N(R^{11})CS$—, —$SON(R^{11})$—, —$SO_2N(R^{11})$—, —$N(R^{11})SO_2$—, —$N(R^{11})CON(R^{11})$—, —$N(R^{11})CSN(R^{11})$—, —$N(R^{11})SON(R^{11})$— and —$N(R^{11})SO_2N(R^{11})$—;

wherein said optional substituents on said alkyl, alkenyl, alkynyl, aliphatic, heteroaliphatic, cycloaliphatic and heterocycloaliphatic groups in $R^2$, $R^3$, $R^5$, $R^{6a}$, $R^7$, $R^8$, $R^9$, $R^{10}$ and $R^{10a}$ are one or more groups selected from halogen, hydroxyl, $C_{1-6}$alkoxy, thiol, $C_{1-6}$alkylthio, —$SC(NH)NH_2$, —$CH_2SC(NH)NH_2$, $NH_2$, —$NR^9R^{10}$, and $C_{3-7}$cyclic amino which is optionally substituted with one to three halogen atoms or $C_{1-4}$alkyl, hydroxyl or $C_{1-4}$alkoxy groups and which optionally contains one or more other heteroatoms or heteroatom containing groups selected from —O—, —S—, —C(O)—, —C(S)—, —S(O)— or —S(O)$_2$—;

wherein said optional substituents on said aryl and heteroaryl groups in $R^7$, $R^8$ and $R^{10a}$ are one or more $R^{12}$ groups, where $R^{12}$ is $R^{13}$ or —Alk($R^{13}$)$_m$;

$R^{13}$ is a halogen atom, —NH$_2$, —NHR$^{14}$, —N(R$^{14}$)$_2$, —NO$_2$, —CN, —OH, —OR$^{14}$, —CHO, —CO$_2$H, —CO$_2$Alk$^1$, —SH, SR$^{14}$, —COR$^{14}$, —CSR$^{14}$, —SO$_3$H, —SO$_2$R$^{14}$, —SO$_2$NH$_2$, —SO$_2$NHR$^{14}$, —SO$_2$N(R$^{14}$)$_2$, —CONH$_2$, —CSNH$_2$, —CONHR$^{14}$, —CSNHR$^{14}$, —CON(R$^{14}$)$_2$, —CSN(R$^{14}$)$_2$, —N(R$^{11}$)SO$_2$H, —N(R$^{11}$)SO$_2$R$^{14}$, —N(SO$_2$R$^{14}$)$_2$, —N(R$^{11}$)SO$_2$NH$_2$, —N(R$^{11}$)SO$_2$NHR$^{14}$, —N(R$^{11}$)SO$_2$N(R$^{14}$)$_2$, —N(R$^{11}$)COR$^{14}$, —N(R$^{11}$)CONH$_2$, —N(R$^{11}$)CONHR$^{14}$, —N(R$^{11}$)CON(R$^{14}$)$_2$, —N(R$^{11}$)CSR$^{14}$, —N(R$^{11}$)CSNH$_2$, —N(R$^{11}$)CSNHR$^{14}$, —N(R$^{11}$)CSN(R$^{14}$)$_2$, —N(R$^{11}$)C(O)OR$^{14}$, optionally substituted $C_{5-7}$cycloalkyl, optionally substituted monocyclic or bicyclic $C_{6-12}$aryl or optionally substituted monocyclic or bicyclic $C_{5-13}$heteroaryl, wherein said cycloalkyl, aryl and heteroaryl substituents are one or two groups selected from $C_{1-6}$alkyl, hydroxyl (—OH), hydroxy$C_{1-6}$alkyl and $C_{1-6}$alkyoxy groups;

$R^{14}$ is —Alk(R$^{13}$)$_m$, hetero$C_{3-6}$cycloalkyl, —Alk-hetero$C_{3-6}$cycloalkyl, monocyclic or bicyclic $C_{6-12}$aryl or monocyclic or bicyclic $C_{1-9}$heteroaryl;

Alk is a straight or branched chain $C_{1-6}$alkylene, $C_{2-6}$alkenylene or $C_{2-6}$alkynylene group optionally interrupted by one, two or three —O— or —S— atoms or —SO—, —S(O)$_2$— or —N(R$^{11}$)— groups;

Alk$^1$ is a straight or branched chain $C_{1-8}$alkyl group which is optionally substituted with one or more $R^{13}$ groups;

Cyc$^1$ is a optionally substituted $C_{3-7}$ monocyclic carbocyclic group optionally containing one or more —O— or —S— atoms or —C(O)—, —C(S), —SO—, —S(O)$_2$— or —N(R$^{11}$)— groups, wherein said optional Cyc$^1$ substituents are selected from one to three halogen atoms or $C_{1-4}$alkyl, hydroxy or $C_{1-4}$alkoxy groups;

m is zero or an integer 1, 2 or 3;

and the salts, solvates, hydrates and N-oxides thereof;

with the provisos that:

(1) when one or both of $R^2$ and $R^3$ is an —OR$^{10}$ group, then $R^1$ is an —OR$^8$ group in which $R^8$ is an optionally substituted $C_{1-10}$aliphatic group substituted by a cyclic amino group, an optionally substituted $C_{1-10}$aliphatic group interrupted with one to four atoms or groups $X^2$, an optionally substituted $C_{3-10}$cycloaliphatic group optionally containing one to four atoms or groups $X^2$, an optionally substituted monocyclic or bicyclic $C_{6-12}$aryl group or an optionally substituted monocyclic or bicyclic $C_{1-9}$heteroaryl group containing one to four heteroatoms selected from oxygen, sulfur or nitrogen atoms;

(2) when $R^5$ is a $C_{1-6}$alkyl or trifluoromethyl group and $R^7$ is a $C_{1-6}$alkyl group optionally substituted with cyano or alkoxy or a $C_{2-6}$alkenyl, $C_{2-6}$alkynyl or —CH$_2$Ar group where Ar is phenyl, then at least one of $R^1$, $R^2$, $R^3$, $R^4$ and $R^6$ is other than a hydrogen atom;

(3) when one of $R^1$, $R^2$ and $R^3$ is bromo, chloro, fluoro, trifluoromethyl, methyl, methoxy, isopropoxy, or trifluoromethoxy and the other of $R^1$, $R^2$ and $R^3$ are hydrogen, chloro, fluoro, methyl or trifluoromethyl, $R^4$ and $R^6$ are hydrogen and $R^7$ is methyl, ethyl, propyl or butyl, then $R^5$ is other than trifluoromethyl; and (4) when $R^4$ and $R^6$ are hydrogen, $R^5$ is hydrogen or methyl and $R^7$ is ethyl, propyl, butyl or —CH$_2$Ar where Ar is phenyl, then at least two of $R^1$, $R^2$ and $R^3$ are other than nitro groups.

11. A method according to claim 10 wherein said disease or disorder is selected from the group consisting of autoimmune diseases, transplant rejection, grant versus host disease, hyperproliferative disorders, and diseases in which cells receive pro-inflammatory signals.

12. A method for the prophylaxis or treatment of a disease or disorder in a mammal in which inappropriate protein tyrosine kinase action plays a role, which comprises administering to a mammal suffering from such a disease or disorder a therapeutically effective amount of a compound selected from the group consisting of:

4-(3-methoxyphenylsulphanyl)-N-{[3,5-dimethyl-4-(2-pyrrolidin-1-yl)-ethoxy]phenyl}-2-pyrimidineamine;

4-(3-carboxyphenylsulphanyl)-N-{[3,5-dimethyl-4-(2-pyrrolidin-1-yl)-ethoxy]phenyl}-2-pyrimidineamine;

N-[4,5-dimethoxy-3-(2-pyrrolidin-1-ylethoxy)phenyl]-4-(3-methoxyphenylsulphanyl)-2-pyrimdineamine;

4-(3-methoxyphenylsulphanyl)-N-{[4-methoxy-[3-(2-pyrrolidin-1-yl)-ethoxy]phenyl}-2-pyrimidineamine;

N-{3,5-dimethoxy-4-[2-pyrrolidin-1-yl)ethoxy]phenyl}-4-(3-methoxyphenylsulphanyl)-2-pyrimdineamine;

N-{[4,5-dimethoxy-3-(2-pyrrolidin-1-yl)ethoxy]phenyl}-4-(4-fluorophenylsulphanyl) pyrimdine-2-amine;

4-(3-bromophenylsulphanyl)-N-[4,5-dimethoxy-3-(2-pyrrolidin-1-yl-ethoxy]phenyl]-2-pyrimidineamine;

N-{3,5-dichloro-4-[2-pyrrolidin-1-yl)ethoxy]phenyl}-4-(3,5-dimethylphenylsulphanyl)-2-pyrimdineamine;

and the salts, solvates, hydrates and N-oxides thereof.

13. A method according to claim 12 wherein the compound is 4-(3-methoxyphenylsulphanyl)-N-{[3,5-dimethyl-4-(2-pyrrolidin-1-yl)-ethoxy]phenyl}-2-pyrimidineamine; and the salts, solvates, hydrates and N-oxides thereof.

14. A method according to claim 12 wherein the compound is 4-(3-carboxyphenylsulphanyl)-N-{[3,5-dimethyl-4-(2-pyrrolidin-1-yl)-ethoxy]phenyl}-2-pyrimidineamine; and the salts, solvates, hydrates and N-oxides thereof.

15. A method according to claim 12 wherein the compound is N-[4,5-dimethoxy-3-(2-pyrrolidin-1-ylethoxy)phenyl]-4-(3-methoxyphenyl-sulphanyl)-2-pyrimdineamine; and the salts, solvates, hydrates and N-oxides thereof.

16. A method according to claim 12 wherein the compound is 4-(3-methoxyphenylsulphanyl)-N-{[4-methoxy-[3-(2-pyrrolidin-1-yl)-ethoxy]phenyl}-2-pyrimidineamine; and the salts, solvates, hydrates and N-oxides thereof.

17. A method according to claim 12 wherein the compound is N-{3,5-dimethoxy-4-[2-pyrrolidin-1-yl)ethoxy]phenyl}-4-(3-methoxyphenyl-sulphanyl)-2-pyrimdineamine; and the salts, solvates, hydrates and N-oxides thereof.

18. A method according to claim 12 wherein the compound is N-{[4,5-dimethoxy-3-(2-pyrrolidin-1-yl)ethoxy]phenyl}-4-(4-fluorophenyl-sulphanyl) pyrimdine-2-amine; and the salts, solvates, hydrates and N-oxides thereof.

19. A method according to claim 12 wherein the compound is 4-(3-bromophenylsulphanyl)-N-[4,5-dimethoxy-3-(2-pyrrolidin-1-yl-ethoxy]phenyl]-2-pyrimidineamine; and the salts, solvates, hydrates and N-oxides thereof.

20. A method according to claim 12 wherein the compound is N-{3,5-dichloro-4-[2-pyrrolidin-1-yl)ethoxy]phenyl}-4-(3,5-dimethylphenyl-sulphanyl)-2-pyrimdineamine; and the salts, solvates, hydrates and N-oxides thereof.

\* \* \* \* \*